United States Patent
Nakai et al.

(10) Patent No.: US 12,122,121 B2
(45) Date of Patent: *Oct. 22, 2024

(54) FLEXIBLE TUBE FOR ENDOSCOPE, ENDOSCOPIC MEDICAL DEVICE, AND METHODS FOR PRODUCING THE SAME

(71) Applicant: FUJIFILM Corporation, Tokyo (JP)

(72) Inventors: Yoshihiro Nakai, Ashigarakami-gun (JP); Toshihide Yoshitani, Ashigarakami-gun (JP); Shinya Abe, Ashigarakami-gun (JP); Kazuma Horita, Ashigarakami-gun (JP); Takeshi Senga, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 701 days.

This patent is subject to a terminal disclaimer.

(21) Appl. No.: 17/343,883

(22) Filed: Jun. 10, 2021

(65) Prior Publication Data

US 2021/0290034 A1     Sep. 23, 2021

Related U.S. Application Data

(63) Continuation of application No. PCT/JP2020/000875, filed on Jan. 14, 2020.

(30) Foreign Application Priority Data

Jan. 16, 2019  (JP) ................ 2019-005383

(51) Int. Cl.
    *B32B 15/08*      (2006.01)
    *A61B 1/00*       (2006.01)
    (Continued)

(52) U.S. Cl.
    CPC .......... *B32B 15/08* (2013.01); *A61B 1/0011* (2013.01); *A61B 1/00135* (2013.01); *B32B 1/08* (2013.01);
    (Continued)

(58) Field of Classification Search
    CPC ... C22C 38/18; A61B 1/0011; A61B 1/00135; A61B 1/005; B32B 1/08; B32B 15/08;
    (Continued)

(56) References Cited

U.S. PATENT DOCUMENTS

| 6,350,799 B1 | 2/2002 | Wang |
| 2003/0207986 A1 | 11/2003 | Wang |

(Continued)

FOREIGN PATENT DOCUMENTS

| CN | 101155542 A | 4/2008 |
| CN | 103703096 A | 4/2014 |

(Continued)

OTHER PUBLICATIONS

Chinese Office Action dated Sep. 9, 2023 in Application No. 202080007418.9.

(Continued)

*Primary Examiner* — James C Yager
(74) *Attorney, Agent, or Firm* — Sughrue Mion, PLLC

(57) ABSTRACT

Provided are a flexible tube for an endoscope, the flexible tube having a flexible tube base made of metal, a resin cover layer that covers an outer periphery of the flexible tube base, and a primer layer that includes a silane coupling agent with a specific structure having an amino group and that is disposed between the flexible tube base and the resin cover layer, in which the resin cover layer includes at least one compound selected from the group consisting of polyamides, polyesters, and polyolefins on a side of the resin cover layer in contact with the primer layer, an endoscopic medical device including the flexible tube for an endoscope, a method for producing the flexible tube for an endoscope, and a method for producing the endoscopic medical device.

12 Claims, 4 Drawing Sheets

(51) Int. Cl.
   *B32B 1/08* (2006.01)
   *B32B 15/18* (2006.01)
   *B32B 27/08* (2006.01)
   *B32B 27/32* (2006.01)
   *A61B 1/005* (2006.01)
   *B32B 27/34* (2006.01)
   *B32B 27/36* (2006.01)

(52) U.S. Cl.
   CPC .............. *B32B 15/18* (2013.01); *B32B 27/08* (2013.01); *A61B 1/005* (2013.01); *B32B 27/32* (2013.01); *B32B 27/34* (2013.01); *B32B 27/36* (2013.01); *B32B 2307/7376* (2023.05); *B32B 2535/00* (2013.01); *Y10T 428/1393* (2015.01)

(58) Field of Classification Search
   CPC ......... B32B 15/18; B32B 27/08; B32B 27/32; B32B 27/34; B32B 27/36; B32B 2307/7376; B32B 2535/00; G02B 23/24; Y10T 428/1393
   See application file for complete search history.

(56) References Cited

U.S. PATENT DOCUMENTS

| | | | |
|---|---|---|---|
| 2010/0036201 A1 | 2/2010 | Ogura | |
| 2011/0056397 A1 | 3/2011 | Nshikawa et al. | |
| 2016/0088998 A1* | 3/2016 | Nagai | A61B 1/0055 156/60 |

FOREIGN PATENT DOCUMENTS

| | | | |
|---|---|---|---|
| CN | 105074306 A | | 11/2015 |
| CN | 105455764 A | | 4/2016 |
| JP | 10-317159 A | | 12/1998 |
| JP | 2002-224018 A | | 8/2002 |
| JP | 2002-224021 A | | 8/2002 |
| JP | 2003-534440 A | | 11/2003 |
| JP | 2005329229 A | * | 12/2005 |
| JP | 2010-035923 A | | 2/2010 |
| JP | 2011-056710 A | | 3/2011 |
| JP | 2015-214743 A | | 12/2015 |
| JP | 2016-067566 A | | 5/2016 |
| WO | 2019/013243 A1 | | 1/2019 |

OTHER PUBLICATIONS

Communication dated Feb. 8, 2022, issued by the Japanese Patent Office in application No. 2020-566411.
International Search Report dated Mar. 10, 2020 from the International Searching Authority in International Application No. PCT/JP2020/000875.
Written Opinion dated Mar. 10, 2020 from the International Searching Authority in International Application No. PCT/JP2020/000875.
International Preliminary Report on Patentability dated Jun. 16, 2021 with translation of the Written Opinion from the International Bureau in International Application No. PCT/JP2020/000875.
Office Action dated Aug. 9, 2022 issued by the Japanese Patent Office in Japanese Application No. 2021-566411.
Communication dated Aug. 15, 2023, issued in Japanese Application No. 2022-179288.

* cited by examiner

FLEXIBLE TUBE FOR ENDOSCOPE, ENDOSCOPIC MEDICAL DEVICE, AND METHODS FOR PRODUCING THE SAME

CROSS-REFERENCE TO RELATED APPLICATIONS

This application is a Continuation of PCT International Application No. PCT/JP2020/000875 filed on Jan. 14, 2020, which claims priority under 35 U.S.C. § 119 (a) to Japanese Patent Application No. 2019-005383 filed in Japan on Jan. 16, 2019. Each of the above applications is hereby expressly incorporated by reference, in its entirety, into the present application.

BACKGROUND OF THE INVENTION

1. Field of the Invention

The present invention relates to a flexible tube for an endoscope, an endoscopic medical device, and methods for producing the same.

2. Description of the Related Art

Endoscopes are medical devices for examining the inside of the body cavity, the inside of the digestive tract, the esophagus, or the like of a patient. Since endoscopes are inserted and used in the body, it is desirable to provide endoscopes that do not damage organs or cause pain or discomfort to a patient. In view of such a requirement, a spiral tube formed by winding a soft, bendable metal strip in a spiral form is adopted as a flexible tube that forms an insertion section (structural section to be inserted into a body cavity) of an endoscope. Furthermore, the periphery of the spiral tube is covered with a flexible resin, and this resin cover layer is covered with a topcoat layer, as needed, so that the spiral tube does not cause stimulation or damage to an inner surface of, for example, the esophagus, digestive tract, or body cavity.

The resin cover layer can be formed by, for example, extrusion-molding a resin on an outer peripheral surface of a flexible tube base that is formed by covering a spiral tube with a tubular mesh. In this case, it is preferable to make the distal end side soft so as to easily insert the flexible tube into the body and to make the proximal end side hard so as to easily perform the operation. In consideration of this point, it has been proposed that a two-layer structure having an inner layer and an outer layer that have different degrees of hardness is adopted as the resin cover layer, and a ratio of the thickness of the inner layer to the thickness of the outer layer is changed in the axial direction of the flexible tube.

Requirements for durability and the like of flexible tubes for endoscopes have been enhanced year by year.

For example, a flexible tube for an endoscope is inserted into a body and used in the inserted state while being, for example, bent or rotated. Therefore, in view of an improvement in durability of a flexible tube for an endoscope, it is important that the flexible tube for an endoscope can maintain adhesiveness between a flexible tube base and a resin cover layer that covers this flexible tube base even when the flexible tube is subjected to such a movement. That is, a flexible tube for an endoscope is required to have the property that a crease, floating, tearing, separation, twisting, or the like is less likely to occur in a resin cover layer even when bending or the like is repeated. If the adhesiveness between the flexible tube base and the resin cover layer is impaired, for example, the surface of the flexible tube inserted in the body catches the peripheral tissues, which may cause a pain to a subject. JP2002-224018A discloses a flexible tube for an endoscope in which a urethane having a terminal treated with a silane coupling agent is used as a material for bonding a flexible tube base to a resin layer serving as an outer cover in order to enhance elasticity and durability.

In addition, flexible tubes for endoscopes are subjected to high-level disinfection treatment in order to prevent infectious diseases. It is known that such high-level cleaning treatment also decreases the adhesiveness between a flexible tube base and a resin cover layer. Techniques to address this problem have also been reported. For example, JP2010-035923A discloses, as a flexible tube for an endoscope to which resistance to disinfection is imparted by increasing water impermeability, a flexible tube for an endoscope in which a silane, titanium, aluminum, or zirconium-based silane coupling agent is applied to a metal core member.

SUMMARY OF THE INVENTION

An object of the present invention is to provide a flexible tube for an endoscope, the flexible tube being capable of sufficiently maintaining adhesiveness between a flexible tube base and a resin cover layer that covers the flexible tube base even when a bending operation is repeated and being less likely to undergo a decrease in the adhesiveness between the flexible tube base and the resin cover layer even when the flexible tube is subjected to high-level disinfection treatment and to provide an endoscopic medical device that includes the flexible tube for an endoscope. Another object of the present invention is to provide a method for producing the flexible tube for an endoscope and a method for producing the endoscopic medical device.

The inventors of the present invention have conducted extensive studies on formation of a resin cover layer in a flexible tube for an endoscope. As a result, the inventors have found that the above objects can be achieved by forming a primer layer that includes a silane coupling agent with a specific structure having an amino group on a surface of a flexible tube base formed of a metal material, and using a specific polymer as a constituent material of a resin cover layer that is in contact with the primer layer. The inventors have further conducted studies on the basis of these findings and completed the present invention.

The objects of the present invention have been achieved by the following means.

[1]
A flexible tube for an endoscope, the flexible tube having a flexible tube base containing metal as a constituent material; a resin cover layer that covers an outer periphery of the flexible tube base; and a primer layer that includes a compound represented by general formula (1) and that is disposed between the flexible tube base and the resin cover layer,
in which the resin cover layer includes at least one compound selected from the group consisting of polyamides, polyesters, and polyolefins at least on a side of the resin cover layer in contact with the primer layer.

General formula (1)

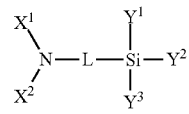

X[1] and X[2] each represent a hydrogen atom, an alkyl group, a cycloalkyl group, an alkenyl group, an aryl group, an acyl group, an alkoxycarbonyl group, or a carbamoyl group.

Y[1] represents a hydroxy group or an alkoxy group. Y[2] and Y[3] each represent a hydrogen atom, a halogen atom, a hydroxy group, an alkoxy group, an oxime group, or an alkyl group.

L represents a single bond, a divalent group selected from the group consisting of alkylene groups, arylene groups, and —O—, or a divalent group which is a combination of two or more selected from the group consisting of the aforementioned divalent groups.

X[1] and X[2] may be linked to each other to form a ring.

[2]

The flexible tube for an endoscope according to [1], in which the compound represented by general formula (1) has two or more nitrogen atoms.

[3]

The flexible tube for an endoscope according to [1] or [2], in which the metal that constitutes the flexible tube base is stainless steel.

[4]

The flexible tube for an endoscope according to any one of [1] to [3], in which the metal that constitutes the flexible tube base has a passivation film on a surface thereof.

[5]

The flexible tube for an endoscope according to any one of [1] to [4], in which the resin cover layer has a single-layer structure or a multilayer structure and includes at least one compound selected from the group consisting of polyamides, polyesters, and polyolefins in a layer in contact with the primer layer.

[6]

The flexible tube for an endoscope according to any one of [1] to [5], in which the resin cover layer has a two-layer structure, and a ratio of a thickness of an inner layer to a thickness of an outer layer of the two-layer structure changes in a gradient manner in an axial direction of the flexible tube base.

[7]

The flexible tube for an endoscope according to [6], in which the ratio of the thickness of the inner layer to the thickness of the outer layer is inner layer:outer layer=95:5 to 60:40 at one end of the flexible tube for an endoscope and is inner layer:outer layer=5:95 to 40:60 at the other end.

[8]

An endoscopic medical device having the flexible tube for an endoscope according to any one of [1] to [7].

[9]

A method for producing a flexible tube for an endoscope, the method including:
a step of forming, on at least an outer periphery of a flexible tube base that contains metal as a constituent material, a primer layer that includes a compound represented by general formula (1); and
a step of forming a resin cover layer, the step including covering, with a resin that includes at least one compound selected from the group consisting of polyamides, polyesters, and polyolefins, the primer layer formed on the outer periphery of the flexible tube base so as to be in contact with the primer layer.

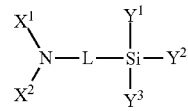

General formula (1)

X[1] and X[2] each represent a hydrogen atom, an alkyl group, a cycloalkyl group, an alkenyl group, an aryl group, an acyl group, an alkoxycarbonyl group, or a carbamoyl group.

Y[1] represents a hydroxy group or an alkoxy group. Y[2] and Y[3] each represent a hydrogen atom, a halogen atom, a hydroxy group, an alkoxy group, an oxime group, or an alkyl group.

L represents a single bond, a divalent group selected from the group consisting of alkylene groups, arylene groups, and —O—, or a divalent group which is a combination of two or more selected from the group consisting of the aforementioned divalent groups.

X[1] and X[2] may be linked to each other to form a ring.

[10]

The method for producing a flexible tube for an endoscope according to [9], in which the resin cover layer has a two-layer structure, at least an inner layer of the two-layer structure includes at least one compound selected from the group consisting of polyamides, polyesters, and polyolefins, and a ratio of a thickness of the inner layer to a thickness of an outer layer of the two-layer structure changes in a gradient manner in an axial direction of the flexible tube base.

[11]

A method for producing an endoscopic medical device, including:
a step of producing a flexible tube for an endoscope by the method for producing a flexible tube for an endoscope according to [9] or [10]; and
a step of incorporating the produced flexible tube for an endoscope into an insertion section of an endoscopic medical device.

[12]

A method for producing an endoscopic medical device, including incorporating the flexible tube for an endoscope according to any one of [1] to [7] into an insertion section of an endoscopic medical device.

In the present invention, when a plurality of substituents, linking groups, or the like (hereinafter referred to as substituents or the like) represented by specific symbols are present or a plurality of substituents or the like are defined simultaneously or alternatively, the substituents or the like may be the same or different from each other. In addition, even if not specifically stated, when a plurality of substituents or the like are adjacent to each other, they may be linked or fused to each other to form a ring.

In the present invention, the term "group" of each group described as an example of a substituent is meant to include both an unsubstituted form and a form having a substituent. For example, the term "alkyl group" means an alkyl group which may have a substituent. When the number of carbon atoms of a group is specified, the number of carbon atoms of this group means the total number of carbon atoms including a substituent, unless otherwise noted.

In the present invention, the designations of compounds are meant to include the compounds themselves, salts thereof, and ions thereof. These designations are also meant to include derivatives formed by changing a part of the structure within the range in which the effects of the present invention are not impaired. Furthermore, if it is not explicitly specified whether a compound is substituted or unsubstituted, it is meant that the compound may have any substituent within the range in which the effects of the present invention are not impaired. This also applies to substituents and linking groups.

In the present invention, the term "(meth)acrylate" is meant to include one or both of acrylate and methacrylate. This also applies to "(meth)acrylic acid", "(meth)acrylamide", "(meth)acrylonitrile", and "(meth)acryloyl group".

In the present invention, any numerical range expressed by using the word "to" means a range including the numerical values before and after the word "to" as the lower and upper limits thereof.

The flexible tube for an endoscope according to the present invention is capable of sufficiently maintaining adhesiveness between a flexible tube base and a resin cover layer that covers the flexible tube base even when a bending operation is repeated, is less likely to undergo a decrease in the adhesiveness between the flexible tube base and the resin cover layer even when the flexible tube is subjected to high-level disinfection treatment, and has good bending durability and good chemical resistance.

According to the endoscopic medical device according to the present invention, a flexible tube which is a structural section to be inserted into a body has good bending durability and good chemical resistance. Therefore, in the endoscopic medical device according to the present invention, the load on a subject during use can be further reduced.

The method for producing a flexible tube for an endoscope according to the present invention can provide a flexible tube for an endoscope, the flexible tube having good bending durability and good chemical resistance.

According to the method for producing an endoscopic medical device according to the present invention, a flexible tube that forms this device can have good bending durability and good chemical resistance. Therefore, the method for producing an endoscopic medical device according to the present invention can provide an endoscopic medical device in which the load on a subject during use is further reduced.

DESCRIPTION OF THE PREFERRED EMBODIMENTS

Figure 1:
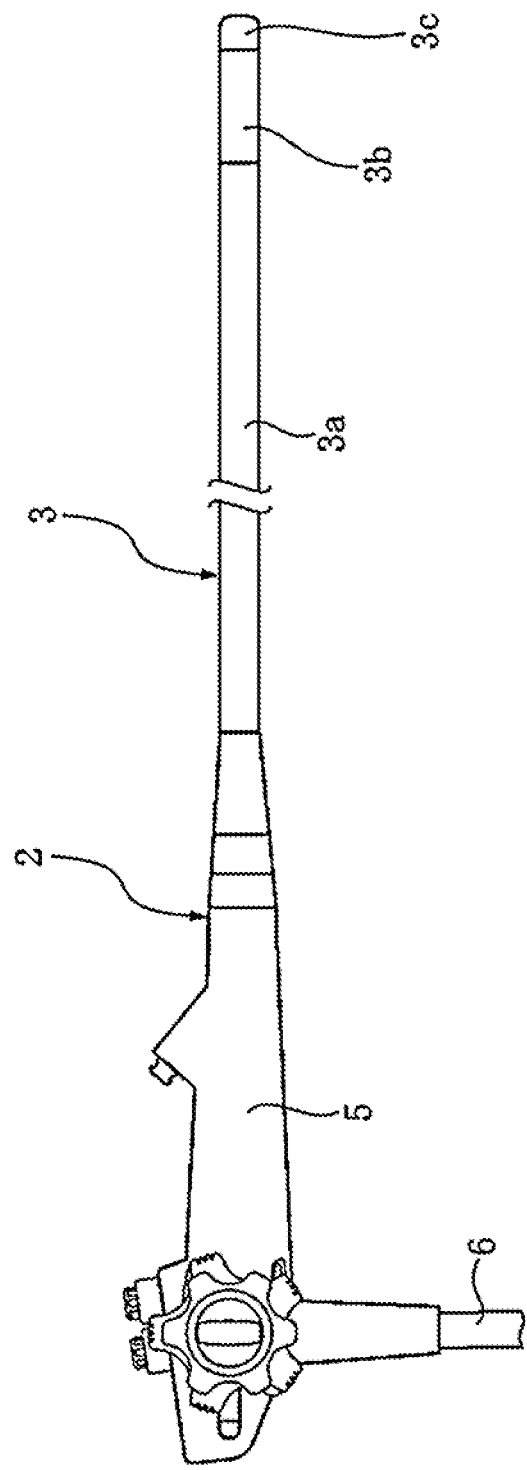
FIG. 1 is an external view illustrating a configuration of an electronic endoscope according to an embodiment.

An electronic endoscope will now be described as an example of an endoscopic medical device according to a preferred embodiment of the present invention. An electronic endoscope includes a flexible tube for an endoscope (hereinafter, a flexible tube for an endoscope may be simply referred to as a "flexible tube"), the flexible tube being incorporated in the electronic endoscope, and is used as a medical device for, for example, examining the inside of the body by inserting the flexible tube into the inside of the body cavity, the inside of the digestive tract, the esophagus, or the like. In the example illustrated in FIG. 1, an electronic endoscope 2 includes an insertion section 3 to be inserted into a body, a main body operating section 5 that is connected to a proximal end portion of the insertion section 3, and a universal cord 6 to be connected to a processor device or a light source device. The insertion section 3 includes a flexible tube 3a connected to the main body operating section 5, an angle portion 3b connected to the flexible tube 3a, and a tip portion 3c which is connected to the distal end of the angle portion 3b and in which an imaging device (not shown) for imaging the inside of the body is installed. The flexible tube 3a that accounts for a large portion of the length of the insertion section 3 has flexibility across substantially the entire length thereof and is configured so that, in particular, a portion to be inserted into the inside of a body cavity or the like has higher flexibility.

Flexible Tube Base

The flexible tube has, as an innermost layer, a flexible tube base containing metal as a constituent material.

Figure 2:
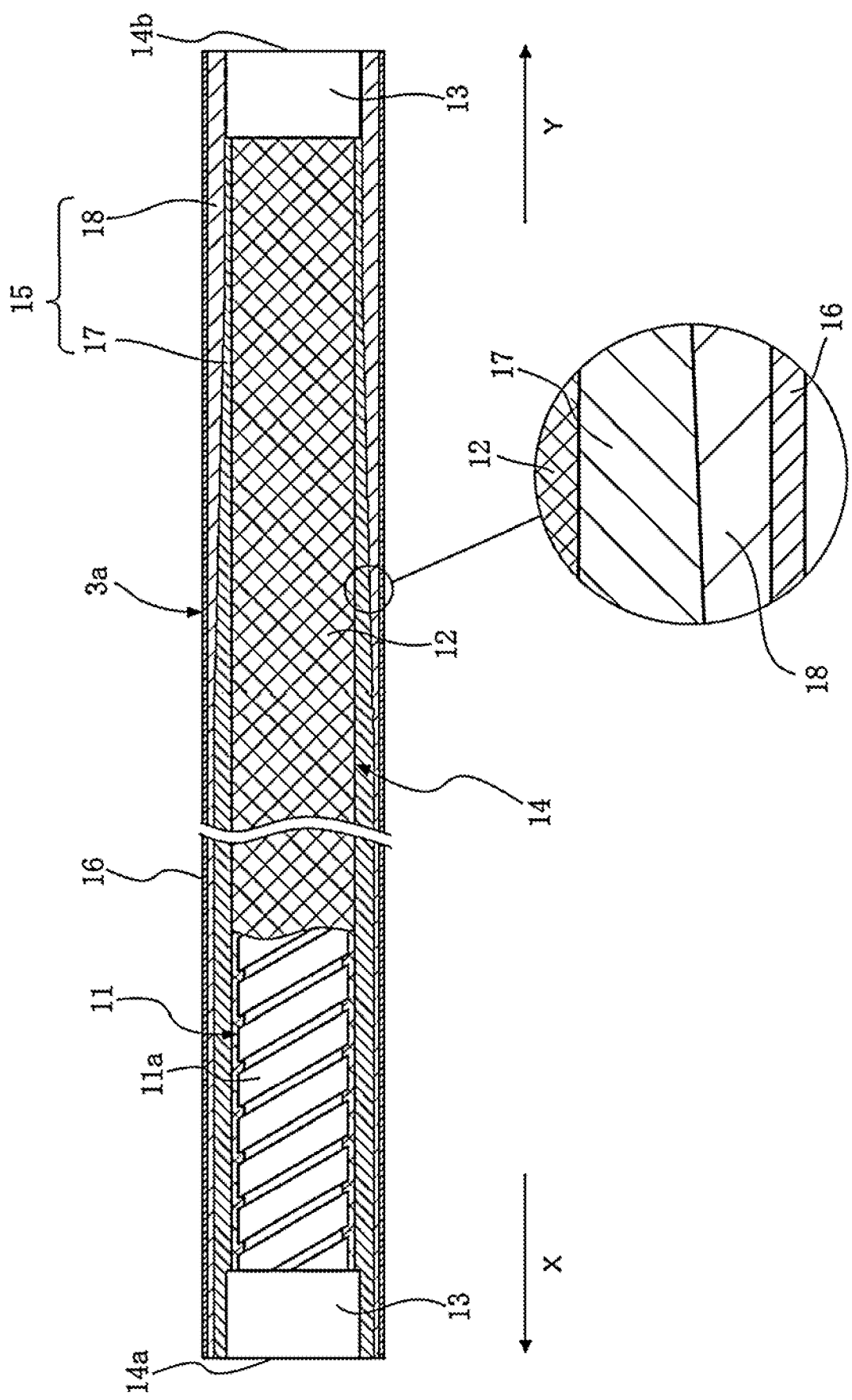
FIG. 2 is a partial sectional view illustrating a configuration of a flexible tube for an endoscope according to an embodiment.

As illustrated in FIG. 2, a flexible tube base 14 preferably has a form in which a spiral tube 11 that is formed, on the innermost side, by winding a metal strip 11a in a spiral form is covered with a tubular mesh 12 obtained by braiding metal wires, and caps 13 are fitted in both ends of the resulting product. The metal constituting the flexible tube base 14 preferably has a surface that has been subjected to passivation treatment in order to prevent corrosion. That is, the flexible tube base 14 preferably has a passivation film on an outer periphery (surface) thereof. This passivation treatment can be performed by an ordinary method. A passivation film can be formed on a surface of metal by, for example, immersing the metal in a solution including a strong oxidizing agent such as nitric acid, heating the metal in air (oxygen) or water (water vapor), or anodizing the metal in a solution including an oxidizing agent.

The metal that constitutes the flexible tube base 14 is preferably stainless steel. The surface of stainless steel is usually in a state in which chromium and oxygen ($O_2$) are bound to each other to form a passivation film. However, even in the case where stainless steel is used as the constituent material of the flexible tube base 14, the stainless steel is preferably subjected to the passivation treatment described above so that a more uniform passivation film is more reliably formed over the entire surface of the stainless steel.

Primer Layer

In the present invention, a primer layer (not shown) is disposed on an outer periphery of the flexible tube base. By disposing this primer layer, it is possible to effectively enhance adhesiveness between the flexible tube base and a resin cover layer described below and provided to cover the outer periphery of the flexible tube base. In the present invention, this primer layer includes a compound represented by general formula (1) below.

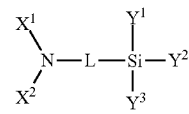

General Formula (1)

In general formula (1), $X^1$ and $X^2$ each represent a hydrogen atom, an alkyl group, a cycloalkyl group, an alkenyl group, an aryl group, an acyl group, an alkoxycarbonyl group, or a carbamoyl group.

The alkyl group that may be employed as $X^1$ and $X^2$ may be linear or branched. The number of carbon atoms of this alkyl group is preferably an integer of 1 to 20, more preferably 1 to 15, still more preferably 1 to 10, and particularly preferably 1 to 8.

Specific examples of the alkyl group that may be employed as $X^1$ and $X^2$ include methyl, ethyl, n-propyl, isopropyl, n-butyl, sec-butyl, isobutyl, tert-butyl, n-pentyl, n-hexyl, n-heptyl, and n-octyl.

The number of carbon atoms of the cycloalkyl group that may be employed as $X^1$ and $X^2$ is preferably 3 to 20, more preferably 3 to 15, still more preferably 3 to 10, and particularly preferably 3 to 8. Specific examples of the cycloalkyl group that may be employed as $X^1$ and $X^2$ include cyclopentyl and cyclohexyl.

The alkenyl group that may be employed as $X^1$ and $X^2$ may be linear or branched. The number of carbon atoms of this alkenyl group is preferably an integer of 2 to 20, more preferably 2 to 15, still more preferably 2 to 10, and particularly preferably 2 to 5.

The number of carbon atoms of the aryl group that may be employed as $X^1$ and $X^2$ is preferably an integer of 6 to 20, more preferably 6 to 15, still more preferably 6 to 12, and particularly preferably 6 to 10.

Specific examples of the aryl group that may be employed as $X^1$ and $X^2$ include phenyl and naphthyl. The aryl group is preferably phenyl.

The number of carbon atoms of the acyl group that may be employed as $X^1$ and $X^2$ is preferably an integer of 2 to 40, more preferably 2 to 30, still more preferably 2 to 20, and particularly preferably 2 to 15.

In the present invention, the term "acyl group" is meant to include a formyl group, alkylcarbonyl groups, and arylcarbonyl groups. The acyl group that may be employed as $X^1$ and $X^2$ is preferably an alkylcarbonyl group or an arylcarbonyl group.

The number of carbon atoms of the alkoxycarbonyl group that may be employed as $X^1$ and $X^2$ is preferably an integer of 2 to 40, more preferably 2 to 30, still more preferably 2 to 20, and particularly preferably 2 to 15.

The number of carbon atoms of the carbamoyl group that may be employed as $X^1$ and $X^2$ is preferably an integer of 1 to 40, more preferably 1 to 30, still more preferably 1 to 20, and particularly preferably 1 to 15.

The alkyl group, the cycloalkyl group, the alkenyl group, the aryl group, the acyl group, the alkoxycarbonyl group, and the carbamoyl group that may be employed as $X^1$ and $X^2$ may each have a substituent.

The substituent which may be included in each of the groups that may be employed as $X^1$ and $X^2$ is not particularly limited as along as the effects of the present invention are not impaired. Examples of the substituent include alkyl groups, cycloalkyl groups, alkenyl groups, alkynyl groups, aryl groups, heterocyclic groups (aromatic heterocyclic groups and aliphatic heterocyclic groups), alkoxy groups, alkylsulfanyl groups, an amino group, acyl groups, alkylcarbonyloxy groups, aryloxy groups, alkoxycarbonyl groups, aryloxycarbonyl groups, acylamino groups, a sulfonamide group, a carbamoyl group, a silyl group, a sulfamoyl group, halogen atoms, a cyano group, a hydroxy group, and a carboxy group. Each of the substituents which may be included in the groups that may be employed as $X^1$ and $X^2$ may be further substituted with a substituent.

The substituent which may be included in each of the groups that may be employed as $X^1$ and $X^2$ is preferably a substituent including at least any one of an amino group, a hydroxy group, or a silyl group and more preferably a substituent including at least an amino group.

The substituent which may be included in each of the groups that may be employed as $X^1$ and $X^2$ is also preferably an amino group, a hydroxy group, or a silyl group and more preferably an amino group.

The amino group may be an unsubstituted amino group or a substituted amino group but is preferably an amino group having at least one hydrogen atom bound to the nitrogen atom and more preferably an unsubstituted amino group ($-NH_2$).

The silyl group may be an unsubstituted silyl group ($-SiH_3$) or a substituted silyl group but is preferably a substituted silyl group. The number of carbon atoms of the whole substituents (when the silyl group has three substituents, the whole of the three substituents) in this substituted silyl group is preferably 1 to 10 and more preferably 1 to 6.

The substituents in the substituted silyl group are preferably each independently a halogen atom, a hydroxy group, an alkoxy group, an oxime group, or an alkyl group and more preferably a hydroxy group, an alkoxy group, or an alkyl group. The number of substituents in the substituted silyl group is not particularly limited. A silyl group having at least one hydroxy group or alkoxy group is preferred.

The halogen atom, the alkoxy group, the oxime group, and the alkyl group that may be employed as the substituents in the substituted silyl group have the same definition as in the halogen atom, the alkoxy group, the oxime group, and the alkyl group that may be employed as $Y^2$ and $Y^3$ described below, and preferred forms thereof are also the same as those of the halogen atom, the alkoxy group, the oxime group, and the alkyl group that may be employed as $Y^2$ and $Y^3$.

The alkyl group, the alkenyl group, the acyl group, the alkoxycarbonyl group, and the carbamoyl group that may be employed as $X^1$ and $X^2$ may each include one or two or more oxygen atoms, nitrogen atoms, or $>C=O$ in the alkyl chain in the group. The type of oxygen atoms, nitrogen atoms, and $>C=O$ that may be included in the alkyl chain may be one or two or more. Note that the expression "included in the alkyl chain" is meant to include not only the form of including in the alkyl chain but also the form of including at a terminal portion of the alkyl chain.

Examples of the alkyl group including an oxygen atom (—O—) in the alkyl chain include [alkyleneoxy], groups and [alkyleneoxy]n-alkylene groups, where n represents the number of repetitions and is preferably 1 to 9, more preferably 3 to 9. Examples of the alkylene include ethylene and isopropylene.

The alkyl group including a nitrogen atom in the alkyl chain is preferably a group including >NR in the alkyl group chain. Examples thereof include alkylene-N(R)-alkylene groups. R represents a hydrogen atom, an alkyl group, or an aryl group. The alkyl group and the aryl group may be substituted with an amino group, a hydroxy group, or a silyl group, and the above description in the amino group and the silyl group can be preferably applied. R is preferably a hydrogen atom.

In addition to the above, for example, the alkyl group including a nitrogen atom and $>C=O$ in the alkyl chain is preferably a group including —N(R)—C(O)— in the alkyl group chain. Examples thereof include alkylene-N(R)—C(O)-alkylene groups. R represents a hydrogen atom, an alkyl group, or an aryl group. The alkyl group and the aryl group may be substituted with an amino group, a hydroxy group, or a silyl group, and the above description in the amino group and the silyl group can be preferably applied. R is preferably a hydrogen atom.

Two or more of the above specific examples may be combined. However, the groups are not limited to the above specific examples.

The compound represented by general formula (1) is interpreted by defining the shortest chain that links a silicon atom to a nitrogen atom (when a plurality of nitrogen atoms are present, the nitrogen atom means a nitrogen atom that forms a chain having the smallest number of atoms linked to the silicon atom) as L, and assigning the substituents in the compound to $X^1$, $X^2$, $Y^1$, to $Y^3$, and L.

$X^1$ and $X^2$ may be linked to each other to form a ring. The number of atoms constituting the ring is preferably 3 to 10, more preferably 4 to 8, and still more preferably 5 or 6. The ring that may be formed by linking $X^1$ and $X^2$ to each other usually includes, as atoms constituting the ring, carbon atoms besides nitrogen atoms. The ring may include two or more nitrogen atoms and may have heteroatoms other than nitrogen atoms. Examples of the heteroatoms other than nitrogen atoms include an oxygen atom, a sulfur atom, and a silicon atom.

The combination of $X^1$ and $X^2$ is preferably a combination of a hydrogen atom and an alkyl group having an unsubstituted amino group as a substituent. The alkyl group having an unsubstituted amino group as a substituent in this preferred combination is preferably a linear alkyl group with a terminal substituted with an unsubstituted amino group, more preferably a linear alkyl group having 1 to 5 carbon atoms with a terminal substituted with an unsubstituted amino group, still more preferably a linear alkyl group having 1 to 4 carbon atoms with a terminal substituted with an unsubstituted amino group, and particularly preferably a linear alkyl group having 1 to 3 carbon atoms with a terminal substituted with an unsubstituted amino group.

In the present invention, the expression "the number of carbon atoms of a linear alkyl group with a terminal substituted with an unsubstituted amino group" means the number of carbon atoms (that is, the number of atoms) constituting a chain that links the unsubstituted amino group at the terminal to the nitrogen atom to which $X^1$ and $X^2$ are bound.

Therefore, when the alkyl group chain includes an oxygen atom (—O—), a nitrogen atom (—NH—), or >C=O, the above expression "the number of carbon atoms of a linear alkyl group with a terminal substituted with an unsubstituted amino group" is read as the number of atoms constituting a chain that links the unsubstituted amino group at the terminal to the nitrogen atom to which $X^1$ and $X^2$ are bound, and applied.

$Y^1$ represents a hydroxy group or an alkoxy group and is preferably an alkoxy group.

Examples of an alkyl group constituting the alkoxy group that may be employed as $Y^1$ include the alkyl groups that may be employed as $X^1$ and $X^2$. Preferred forms of the alkyl group are also the same as those of the alkyl groups that may be employed as $X^1$ and $X^2$.

$Y^2$ and $Y^3$ each represent a hydrogen atom, a halogen atom, a hydroxy group, an alkoxy group, an oxime group, or an alkyl group. The alkoxy group that may be employed as $Y^2$ and $Y^3$ has the same definition as the alkoxy group that may be employed as $Y^1$, and preferred forms of the alkoxy group are also the same as those of the alkoxy group that may be employed as $Y^1$. The alkyl group that may be employed as $Y^2$ and $Y^3$ has the same definition as the alkyl group that may be employed as $X^1$ and $X^2$, and preferred forms of the alkyl group are also the same as those of the alkyl group that may be employed as $X^1$ and $X^2$.

The halogen atom that may be employed as $Y^2$ and $Y^3$ may be a fluorine atom, a chlorine atom, a bromine atom, or an iodine atom and is preferably a chlorine atom or a bromine atom.

The oxime group that may be employed as $Y^2$ and $Y^3$ is a substituent having the following structure.

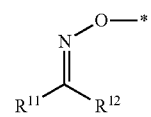

In the above structure, $R^{11}$ and $R^{12}$ each represent a substituent, and * represents a portion bound to a silicon atom.

Examples of the substituent that may be employed as $R^{11}$ and $R^{12}$ include alkyl groups (preferably having 1 to 12 carbon atoms and more preferably having 1 to 8 carbon atoms), alkenyl groups (preferably having 2 to 12 carbon atoms and more preferably having 2 to 8 carbon atoms), alkynyl groups (preferably having 2 to 12 carbon atoms and more preferably having 2 to 8 carbon atoms), aryl groups (preferably having 6 to 20 carbon atoms and more preferably having 6 to 10 carbon atoms), and heterocyclic groups.

The heterocyclic ring constituting the heterocyclic group that may be employed as $R^{11}$ and $R^{12}$ may be a saturated or unsaturated aliphatic heterocyclic ring or an aromatic heterocyclic ring and may be a monocycle or a fused ring. The heterocyclic ring may be a bridged ring. Examples of heteroatoms included in the heterocyclic ring include an oxygen atom, a nitrogen atom, and a sulfur atom. The number of heteroatoms included in one heterocyclic ring is not particularly limited but is preferably 1 to 3 and more preferably 1 or 2. The number of carbon atoms of the heterocyclic ring is preferably 2 to 10 and more preferably 4 or 5. The heterocyclic ring is preferably a three- to seven-membered ring, more preferably a three- to six-membered ring, and still more preferably a three- to five-membered ring.

Examples of the oxime group include a dimethyl ketoxime group, a methyl ethyl ketoxime group, and a diethyl ketoxime group.

At least two of $Y^1$, $Y^2$ and $Y^3$ are each preferably an alkoxy group or a hydroxy group. All of $Y^1$, $Y^2$ and $Y^3$ are each more preferably an alkoxy group or a hydroxy group.

In general formula (1), $X^2$ and $Y^3$ may be linked to each other to form a ring. The number of atoms constituting this ring is preferably 3 to 10, more preferably 4 to 8, and still more preferably 5 or 6. When $X^2$ and $Y^3$ are linked to each other to form a ring, L described below is preferably a single bond. In the ring that may be formed by linking $X^2$ and $Y^3$ to each other, a ring-constituting atom other than a nitrogen atom and a silicon atom is preferably a carbon atom.

L is a single bond, a divalent group selected from the group consisting of alkylene groups, arylene groups, and —O— (an ether bond), or a divalent group which is a combination of two or more selected from the group consisting of alkylene groups, arylene groups, and —O—. When L is a divalent group, the molecular weight of L is preferably 14 to 300 and more preferably 14 to 210.

The alkylene group that may constitute L may be linear or branched. The number of carbon atoms of this alkylene group is preferably an integer of 1 to 20, more preferably 1 to 15, still more preferably 1 to 12, particularly preferably 1 to 10, and most preferably 1 to 8.

The number of carbon atoms of the arylene group that may constitute L is preferably an integer of 6 to 20, more preferably 6 to 15, still more preferably 6 to 12, and particularly preferably 6 to 10. The arylene group that may constitute L is particularly preferably phenylene.

Examples of the divalent group which may be employed as L and which is a combination of two or more selected from the group consisting of alkylene groups, arylene groups, and —O— include alkylene-O-alkylene, alkylene-O-arylene, and alkylene-arylene. The divalent group is preferably alkylene-O-arylene or alkylene-arylene.

The divalent group which is a combination of two or more selected from the group consisting of alkylene groups, arylene groups, and —O— may bind to the nitrogen atom on one side or the other side thereof.

L is preferably an alkylene group, an arylene group, alkylene-O-arylene, or alkylene-arylene, more preferably an alkylene group or alkylene-arylene, and still more preferably an alkylene group.

From the viewpoint of further improving "bending durability", which is a property that adhesiveness between a flexible tube base and a resin cover layer that covers the flexible tube base can be sufficiently maintained even when a bending operation is repeated, and "chemical resistance", which is a property that a decrease in adhesiveness between a flexible tube base and a resin cover layer is less likely occur even when the flexible tube is subjected to high-level disinfection treatment with peracetic acid or the like, the compound represented by general formula (1) is preferably a compound that satisfies any of (i) to (v) below.

(i) In the structure represented by general formula (1), the number of bonds of atoms constituting the shortest chain that links the nitrogen atom to which $X^1$ and $X^2$ are bound to the silicon atom to which $Y^1$ to $Y^3$ are bound (hereinafter, also simply referred to as a "number of atoms constituting the shortest chain") is 1 to 10 and preferably 1 to 6.
(ii) L is a linear alkylene group.
(iii) L is an unsubstituted alkylene group.
(iv) The combination of $X^1$ and $X^2$ is a combination of a hydrogen atom and a linear alkyl group having 1 to 5 carbon atoms with a terminal substituted with an unsubstituted amino group.
(v) The compound has two or more nitrogen atoms therein.

In particular, in the case of considering chemical resistance, it is more preferable to satisfy the (v) above, and a compound that is represented by general formula (1) and that satisfies all the (i) to (v) above is still more preferable.

The compound represented by general formula (1) and constituting the primer layer functions as a silane coupling agent. Specifically, "—Si($Y^1$)($Y^2$)$Y^3$" in general formula (1) interacts with metal that constitutes the flexible tube base, and "—N($X^1$)$X^2$" interacts with any of a polyamide, a polyester, and a polyolefin that constitutes a side of the resin cover layer in contact with the primer layer. It is considered that, as a result, the resin cover layer that covers the outer periphery of the flexible tube base can be firmly brought into close contact with the surface of the flexible tube base to provide a flexible tube for an endoscope, the flexible tube having both good bending durability and good chemical resistance.

An example of the interaction of "—Si($Y^1$)($Y^2$)$Y^3$" with the metal that constitutes the flexible tube base 14 is an adsorption between a hydroxy group produced by hydrolysis of an alkoxy group bound to Si of this group or a hydroxy group bound to Si and an active group, such as a hydroxy group, on the surface of the metal constituting the flexible tube base. This adsorption includes an adsorption that is due to intermolecular force, an ionic bond, and the like and that does not involve a chemical reaction, and an adsorption due to a covalent bond formed by a polycondensation reaction under heating or the like. These two types of adsorptions may coexist. Examples of the group that performs the adsorption with the active group, such as a hydroxy group, on the surface of the metal constituting the flexible tube base include, in addition to the above, hydroxy groups produced by hydrolysis of a hydrogen atom, a halogen atom, or an oxime group bound to Si of the group.

Although the interaction between "—N($X^1$)$X^2$" and any of a polyamide, a polyester, and a polyolefin is not necessarily clear, one possible factor is that, for example, intermolecular force at an organic-organic interface effectively acts.

The compound represented by general formula (1) and used in the present invention contributes to adhesion between the flexible tube base and the resin cover layer in a monomolecular form. The thickness of the primer layer is remarkably smaller than that of a typical adhesive layer (in other words, the concept of the thickness cannot be recalled). That is, the primer layer including the compound represented by general formula (1) differs from such an adhesive layer that requires a certain degree of thickness and softness for adhesion between the flexible tube base and the resin cover layer. Therefore, in fact, the primer layer does not affect the resilience of the flexible tube, and thus the flexible tube according to the present invention also has good resilience.

In the present invention, the expression "a primer layer includes a compound represented by general formula (1)" is meant to include at least one of a form in which the compound represented by general formula (1) is included in a state of having reacted with the flexible tube base or a form in which the compound represented by general formula (1) is included in a state of having reacted with the resin cover layer, or each of the forms. Specifically, at least a portion of a hydrolyzable group bound to Si in the compound represented by general formula (1) is hydrolyzed and a hydroxy group is thereby exposed, and the compound represented by general formula (1) can be present in a state where the exposed hydroxy group reacts with the metal constituting the flexible tube base or an amino group such as "—N($X^1$)$X^2$" reacts with a group on the surface of the resin cover layer.

Alternatively, for example, in the case of a primer layer formed by using a coating liquid, the pH of which has been adjusted to be acidic or alkaline as described below, a portion of the compound represented by general formula (1) may be present in the form of a salt or an ion.

Specific examples of the compound represented by general formula (1) are shown below. However, the present invention is not limited to these examples. In the structures below, Me represents methyl, and Et represents ethyl. The structure in the parentheses in compound S-42 represents a repeating unit with a number of repetitions of 3 to 9.

In the chemical structures below, alkoxy groups are shown as the substituents bound to a silicon atom. Structures in which some or all of the alkoxy groups are replaced by hydroxy groups are also preferable as the compound represented by general formula (1).

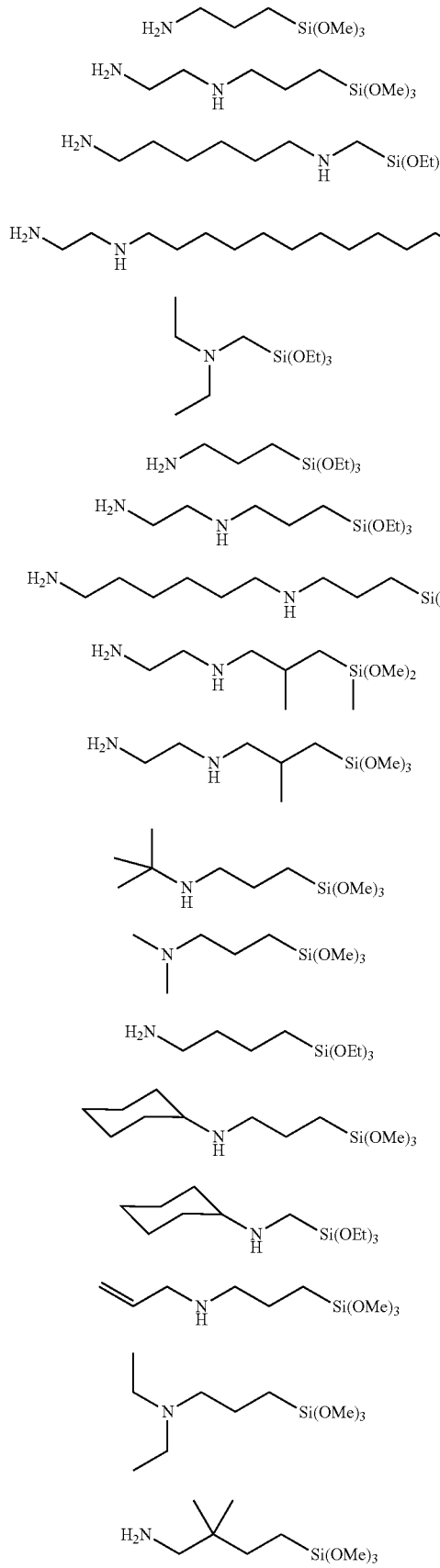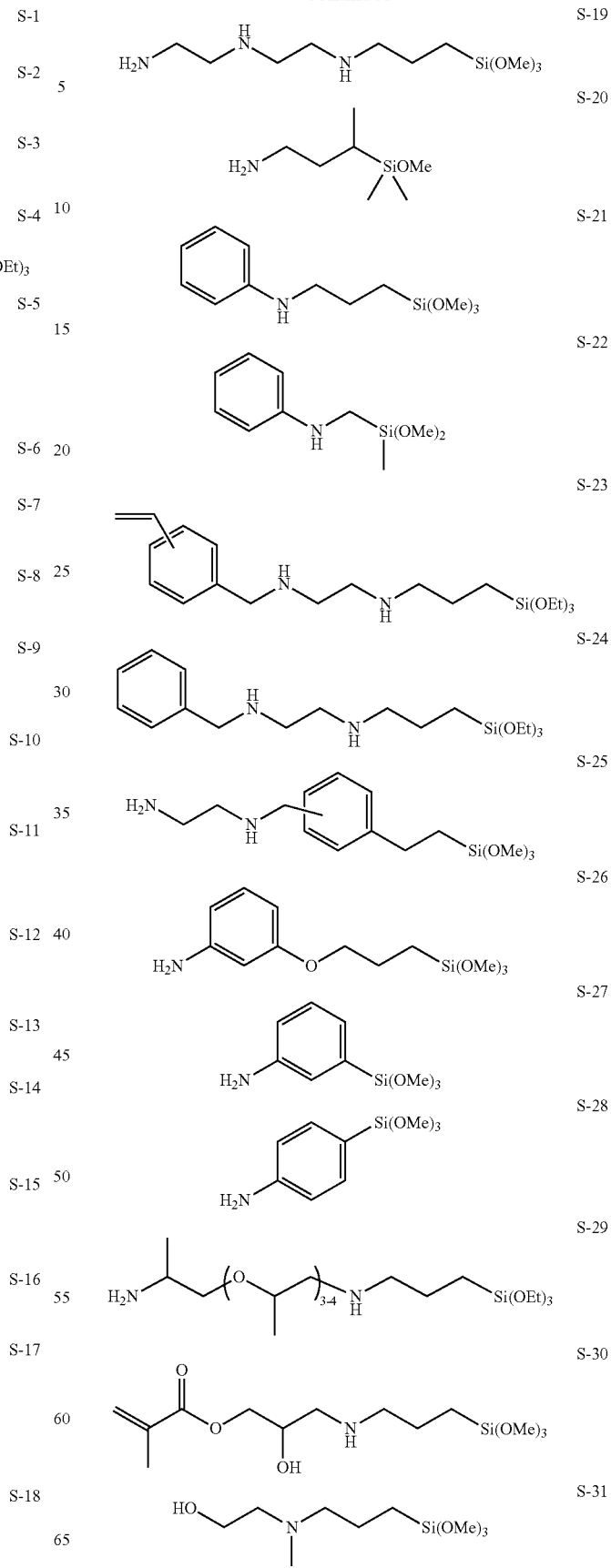

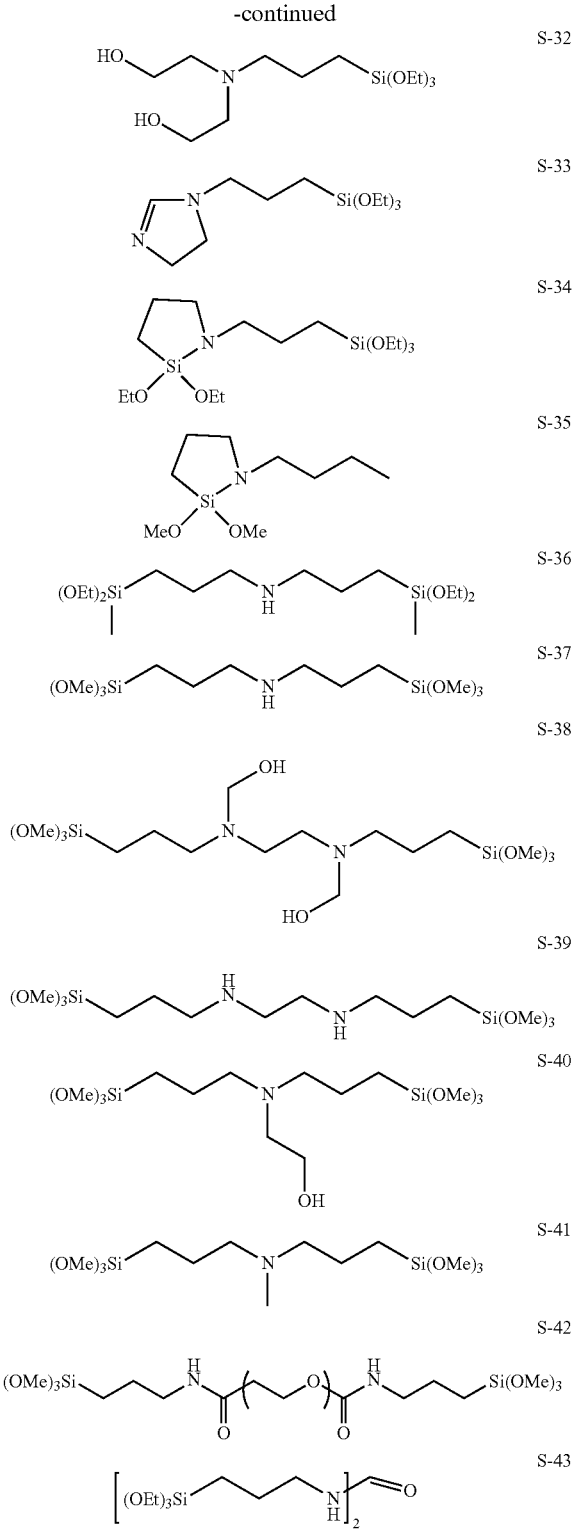

The content of the compound represented by general formula (1) in the primer layer is not particularly limited. However, the lower limit of the content is preferably 90% by mass or more, more preferably 95% by mass or more, still more preferably 97% by mass or more, and particularly preferably 99% by mass or more. The upper limit can be 100% by mass.

The primer layer may contain, besides the compound represented by general formula (1), additives such as a surfactant, a thickener, a leveling agent, a stabilizer, and an antifoaming agent.

Resin Cover Layer

The flexible tube according to the present invention has a resin cover layer on an outer periphery of a flexible tube base having a primer layer thereon.

In the embodiment in FIG. 2, an outer surface of a resin cover layer 15 is coated with a topcoat layer 16 that contains fluorine or the like and that contributes to, for example, chemical resistance. In FIG. 2, a spiral tube 11 is illustrated as a single layer. Alternatively, the spiral tube 11 may be formed by concentrically stacking two or more layers. Note that the resin cover layer 15 and the topcoat layer 16 in the figure are shown to be thicker than the actual thicknesses with respect to the diameter of a flexible tube base 14 for the sake of clearly illustrating the layer structure.

In the present invention, the resin cover layer covers an outer peripheral surface of the flexible tube base having the above-described primer layer thereon. The resin cover layer 15 in the embodiment in FIG. 2 has a two-layer structure in which an inner layer 17 that covers the entire peripheral surface around the axis of the flexible tube base 14 and an outer layer 18 that covers the entire peripheral surface around the axis of the inner layer 17 are stacked. Typically, a soft resin is used as the material of the inner layer 17, and a hard resin is used as the material of the outer layer 18. However, the present invention is not limited to these embodiments.

In the present invention, when the resin cover layer has a multilayer structure having two or more layers, at least the innermost layer (layer that is in contact with the primer layer) includes at least one selected from the group consisting of polyamides, polyesters, and polyolefins, as described below. In the present invention, when the resin cover layer is formed of a single layer, this single-layer resin cover layer includes at least one selected from the group consisting of polyamides, polyesters, and polyolefins. That is, the resin cover layer in the present invention includes at least one compound selected from the group consisting of polyamides, polyesters, and polyolefins at least on the side of the resin cover layer in contact with the primer layer.

The at least one compound selected from the group consisting of polyamides, polyesters, and polyolefins preferably includes at least one compound selected from the group consisting of polyamides and polyesters from the viewpoint of further improving adhesiveness by enhancing the interaction between —N($X^1$)$X^2$ and the polymer (compound) constituting the resin cover layer to achieve better bending durability. It is considered that, when the resin cover layer contains at least one compound selected from the group consisting of polyamides and polyesters, for example, at least any of a hydrogen bond with any of an amide bond and an ester bond, a hydrogen bond with a hydroxy residue in polyamides and polyesters, a covalent bond with a carboxy residue or an amino residue in polyamides and polyesters, or the like is efficiently produced, and the adhesiveness to the resin cover layer can be further improved.

The polyamides, polyesters, and polyolefins included in the resin cover layer are preferably thermoplastic polymers.

From the viewpoint of being capable of easily forming a resin cover layer having a relatively small thickness by a thermal process, the melt volume rate (MVR) of the thermoplastic polymer is preferably 1 $cm^3$/10 min to 100 $cm^3$/10 min, more preferably 2 $cm^3$/10 min to 80 $cm^3$/10 min, and still more preferably 3 $cm^3$/10 min to 60 $cm^3$/10 min.

The MVR is a value measured in accordance with JIS K 7210-1.

Polyamide

Typical polyamides that can be used as a resin cover layer of a flexible tube for an endoscope can be widely employed as the polyamides. Examples thereof include crystalline polyamides, amorphous polyamides, and polyamide elastomers.

Examples of the crystalline polyamides include, but are not particularly limited to, aliphatic polyamides and aromatic polyamides.

Examples of the aliphatic polyamides include poly-ε-caproamide (polyamide 6), polytetramethylene adipamide (polyamide 46), polyhexamethylene adipamide (polyamide 66), polycaproamide/polyhexamethylene adipamide copolymers (polyamide 6/66), polyundecamide (polyamide 11), polycaproamide/polyundecamide copolymers (polyamide 6/11), polydodecamide (polyamide 12), polycaporamide/polydodecamide copolymers (polyamide 6/12), polyhexamethylene sebacamide (polyamide 610), polydecamethylene sebacamide (polyamide 1010), polyhexamethylene dodecamide (polyamide 612), polydecamethylene dodecamide (polyamide 1012), polyundecamethylene adipamide (polyamide 116), and mixtures and copolymers thereof.

Examples of the aromatic polyamides include polyhexamethylene isophthalamide (polyamide 6I), polyhexamethylene terephthalamide (polyamide 6T), polyhexamethylene terephthalamide/polyhexamethylene isophthalamide copolymers (polyamide 6T/6I), polycaproamide/polyhexamethylene terephthalamide copolymers (polyamide 6/6T), polycaproamide/polyhexamethylene isophthalamide copolymers (polyamide 6/6I), polyhexamethylene adipamide/polyhexamethylene terephthalamide copolymers (polyamide 66/6T), polyhexamethylene adipamide/polyhexamethylene isophthalamide copolymers (polyamide 66/6I), polytrimethylhexamethylene terephthalamide (polyamide TMDT), polybis(4-aminocyclohexyl)methane dodecamide (polyamide PACM12), polybis(3-methyl-4-aminocyclohexyl) methane dodecamide (nylon dimethyl PACM12), poly-m-xylylene adipamide (polyamide MXD6), polydecamethylene terephthalamide (polyamide 10T), polyundecamethylene terephthalamide (polyamide 11T), and mixtures and copolymers thereof.

Examples of the amorphous polyamides include polycondensates of isophthalic acid/1,6-hexanediamine/bis(3-methyl-4-aminocyclohexyl)methane, acid/terephthalic polycondensates of terephthalic acid/2,2,4-trimethyl-1,6-hexanediamine/2,4,4-trimethyl-1,6-hexanediamine, polycondensates of isophthalic acid/bis(3-methyl-4-aminocyclohexyl)methane/ω-laurolactam, polycondensates of isophthalic acid/terephthalic acid/1,6-hexanediamine, polycondensates of isophthalic acid/2,2,4-trimethyl-1,6-hexanediamine/2,4,4-trimethyl-1,6-hexanediamine, polycondensates of isophthalic acid/terephthalic acid/2,2,4-trimethyl-1, 6-hexanediamine/2,4,4-trimethyl-1,6-hexanediamine, polycondensates of isophthalic acid/bis(3-methyl-4-aminocyclohexyl)methane/@-laurolactam, and polycondensates of isophthalic acid/terephthalic acid/other diamine components.

Examples of the polyamide elastomers include elastomers containing polyamides as hard segments, the elastomers being called amide-based thermoplastic elastomers. Examples thereof include multiblock copolymers having hard segments composed of polyamides and soft segments composed of polyethers or polyesters, and multiblock copolymers having hard segments composed of polyamides and soft segments having bonding forms of both an ether bond and an ester bond. Examples of the hard segments include polyamide 6, polyamide 66, polyamide 610, polyamide 11, and polyamide 12. Examples of the polyethers for the soft segments include polyethylene glycol, poly(oxytetramethylene) glycol, and poly(oxypropylene) glycol. Examples of the polyesters include poly(ethylene adipate) glycol and poly(butylene-1,4-adipate) glycol.

From the viewpoint of bending durability and peracetic acid resistance, the polyamide used in the present invention is preferably polyamide 1010, polyamide 11, polyamide 12, or a polyamide elastomer.

Examples of commercially available polyamides used in the present invention include polyamide 11 (trade name "Rilsan BMN O" manufactured by Arkema Inc.), polyamide 12 (trade name "DAIAMID L1940" manufactured by Daicel-Evonik Ltd.), polyamide 1010 (trade name "VESTAMID Terra DS16" manufactured by Daicel-Evonik Ltd.), polyamide 1012 (trade name "VESTAMID Terra DD16" manufactured by Evonik), an amorphous polyamide (trade name "TROGAMID CX7323" manufactured by Daicel-Evonik Ltd.), and polyamide elastomers (trade name "PEBAX 7233" and "PEBAX Rnew 80R53" manufactured by Arkema Inc.).

These polyamides may be used alone or in combination of two or more thereof.

Polyester

Typical polyesters that can be used as a resin cover layer of a flexible tube for an endoscope can be widely employed as the polyesters. Examples thereof include thermoplastic polyesters and polyester elastomers.

Examples of the thermoplastic polyesters include polyesters formed from a dicarboxylic acid component and a diol component and polyesters formed from a hydroxycarboxylic acid component.

Examples of the dicarboxylic acid component include terephthalic acid, isophthalic acid, phthalic acid, 2,6-naphthalenedicarboxylic acid, 4,4'-biphenyldicarboxylic acid, 5-sodiosulfoisophthalic acid, oxalic acid, succinic acid, adipic acid, sebacic acid, azelaic acid, dodecanedioic acid, dimer acids, maleic anhydride, maleic acid, fumaric acid, itaconic acid, citraconic acid, mesaconic acid, and cyclohexanedicarboxylic acid.

Examples of the diol component include ethylene glycol, diethylene glycol, 1,3-propanediol, 1,4-butanediol, neopentyl glycol, 1,6-hexanediol, cyclohexanedimethanol, triethylene glycol, polyethylene glycol, polypropylene glycol, polytetramethylene glycol, and ethylene oxide adducts of bisphenol A, bisphenol S, and the like.

Examples of the hydroxycarboxylic acid component include ε-caprolactone, lactic acid, and 4-hydroxybenzoic acid.

The thermoplastic polyesters may be homopolymers formed from the dicarboxylic acid component and the diol component or homopolymers formed from the hydroxycarboxylic acid component, or copolymers formed from the above components. The thermoplastic polyesters may further contain a small amount of a trifunctional or higher compound component such as trimellitic acid, trimesic acid, pyromellitic acid, trimethylolpropane, glycerol, or pentaerythritol.

Examples of the polyester elastomers include elastomers containing polyesters as hard segments, the elastomers being called ester-based thermoplastic elastomers. Examples thereof include multiblock copolymers having hard segments composed of crystalline polyesters and soft segments composed of polyethers or polyesters, and multiblock copolymers having hard segments composed of crystalline polyesters and soft segments having bonding forms of both an ether bond and an ester bond.

Examples of the hard segments include polybutylene terephthalate and polyethylene terephthalate.

Examples of the soft segments include polyalkylene glycols such as polytetramethylene glycol and polypropylene glycol, bisphenol A-ethylene oxide adducts, bisphenol A-propylene oxide adducts, and polyesters such as polycaprolactone.

For example, block copolymers composed of high-melting-point polyester segments (hard segments) and low-melting-point polymer segments (soft segments) having a molecular weight of 400 to 6,000 can be used, as described in, for example, JP1999-92636A (JP-H11-92636A).

To further improve the bending durability, the thermoplastic polyester used in the present invention preferably has a structure derived from polybutylene naphthalate.

Examples of commercially available polyesters used in the present invention include polyester elastomers (trade name "PELPRENE P-70B" and "PELPRENE S-3001" manufactured by Toyobo Co., Ltd.) and (trade name "PRIMALLOY B1942" manufactured by Mitsubishi Chemical Corporation) and polybutylene terephthalate (trade name "NOVADURAN 5505S" manufactured by Mitsubishi Engineering-Plastics Corporation).

These polyesters may be used alone or in combination of two or more thereof.

Polyolefin

Typical polyolefins that can be used as a resin cover layer of a flexible tube for an endoscope can be widely employed as the polyolefins. Examples thereof include polyolefins and olefin-based elastomers.

Examples of the polyolefins include homopolymers and copolymers of α-olefins having 2 to 20 carbon atoms, such as ethylene, propylene, 1-butene, 1-hexene, and 4-methylpentene. Examples thereof further include copolymers of α-olefins and nonconjugated dienes having 2 to 20 carbon atoms, such as dicyclopentadiene, 1,4-hexadiene, cyclooctadiene, methylene norbornene, ethylidene norbornene, butadiene, and isoprene. Examples thereof further include ethylene-α-olefin copolymer rubbers, ethylene-α-olefin-nonconjugated diene copolymer rubbers, propylene-α-olefin copolymer rubbers, and butene-α-olefin copolymer rubbers. It is also possible to use, for example, ethylene-(meth)acrylic acid ester-(meth)acrylic acid copolymers, ethylene-vinyl acetate copolymers, ethylene-vinyl acetate-(meth)acrylic acid copolymers, ethylene-propylene-(meth)acrylic acid copolymers, ethylene-propylene-(meth)acrylic acid ester-(meth)acrylic acid copolymers, ethylene-maleic anhydride copolymers, ethylene-(meth)acrylic acid ester-maleic anhydride copolymers, ethylene-butene-(at least one of maleic anhydride or (meth)acrylic acid) copolymers, propylene-butene-(at least one of maleic anhydride or (meth)acrylic acid) copolymers, ethylene-vinyl chloride copolymers, and ethylene-(meth)acrylic acid copolymers.

The olefin-based elastomers are elastomers including polyolefins as hard segments and rubber components as soft segments, the elastomers being called olefin-based thermoplastic elastomers. Examples of the olefin elastomers include blend-type elastomers, dynamically crosslinked-type elastomers, and polymer-type elastomers of the above polyolefins and rubber components.

Examples of the polyolefins in the olefin-based elastomers include ethylene-propylene copolymers, ethylene-1-butene copolymers, ethylene-α-olefin copolymers, propylene-1-butene copolymers, propylene-α-olefin copolymers, 1-butene-α-olefin copolymers, propylene-1-butene-ethylene copolymers, propylene-α-olefin-ethylene copolymers, propylene-α-olefin-1-butene copolymers, 1-butene-α-olefin-ethylene copolymers, and polypropylene.

Examples of the rubber components in the olefin-based elastomers include isoprene rubber (IR), butadiene rubber (BR), chloroprene rubber (CR), butyl rubber (IIR, i.e., isobutylene-isoprene copolymers), propylene rubber (PP), ethylene-propylene rubber (EPM), and ethylene-propylene-diene rubber (EPDM).

The olefin-based elastomers may contain one of the polyolefins alone or two or more of the polyolefins in combination and may contain one of the rubber components alone or two or more of the rubber components in combination.

Examples of commercially available polyolefins used in the present invention include an olefin-based elastomer (trade name "SARLINK 3145D" manufactured by Toyobo Co., Ltd.).

These polyolefins may be used alone or in combination of two or more thereof.

The total amount of polymers selected from the group consisting of polyamides, polyesters, and polyolefins contained in the resin cover layer in the case of a single-layer resin cover layer, and the total amount of polymers selected from the group consisting of polyamides, polyesters, and polyolefins contained in the innermost layer in the case of a multilayer resin cover layer are each preferably 50% by mass or more, more preferably 70% by mass or more, still more preferably 80% by mass or more, and still more preferably 90% by mass or more. When the resin cover layer is formed of a single layer, the resin cover layer may be a layer composed of at least one selected from the group consisting of polyamides, polyesters, and polyolefins. When the resin cover layer is formed of a plurality of layers, the innermost layer may be a layer composed of at least one selected from the group consisting of polyamides, polyesters, and polyolefins.

When the resin cover layer in the case of a single-layer resin cover layer and the innermost layer in the case of a multilayer resin cover layer include a polymer other than polyamides, polyesters, and polyolefins, the polymer is not particularly limited as long as the effects of the present invention are not impaired. Examples of the other polymer include polyurethanes.

Polyurethane

Typical polyurethanes that can be used as a resin cover layer of a flexible tube for an endoscope can be widely employed as polyurethanes that can be used as the resin cover layer. For example, carbonate-based, ether-based, or ester-based polyurethanes, or mixed polyurethanes of these can be used. Polyurethane elastomers are also preferred. The polyurethane elastomers may be block polymers including hard segments composed of polyurethanes and soft segments having an ether, ester, or carbonate bond or a mixed form of these bonds, the block polymers being called urethane-based thermoplastic elastomers. Such polyurethane elastomers can be appropriately prepared depending on the purpose. Examples thereof include block polymers including hard segments composed of low-molecular-weight glycol components and diisocyanate components and soft segments composed of high-molecular-weight (long-chain) diol components and diisocyanate components.

Examples of the high-molecular-weight (long-chain) diol components include polyether diols, polyester diols, and lactone-based polyester diols. Examples thereof include polypropylene glycol, polytetramethylene oxide, poly(1,4-butylene adipate), poly(ethylene adipate-co-1,4-butylene adipate), polycaprolactone-based diol, poly(1,6-hexylene carbonate), and poly(1,6-hexylene adipate-co-neopentylene adipate). The high-molecular-weight (long-chain) diols preferably have a number-average molecular weight of 500 to 10,000.

As the low-molecular-weight glycol components, short-chain diols such as ethylene glycol, propylene glycol, 1,4-butanediol, and bisphenol A can be used. The short-chain diols preferably have a number-average molecular weight of 48 to 500.

Examples of the diisocyanate components include diphenylmethane diisocyanate, hexamethylene diisocyanate, tolidine diisocyanate, 1,5-naphthalene diisocyanate, isophorone diisocyanate, and xylylene diisocyanate.

For the polyurethane elastomers according to the above embodiment, disclosure of, for example, JP2005-015643A can be referred to.

Examples of commercially available polyurethanes include PANDEX T-2185 and T-2983N (which are manufactured by DIC Corporation), Miractran (manufactured by Nippon Miractran Co., Ltd.), Elastollan (manufactured by BASF Japan Ltd.), RESAMINE (manufactured by Dainichiseika Color & Chemicals Mfg. Co., Ltd.), Pellethane (manufactured by Dow Chemical Japan Ltd.), Iron Rubber (manufactured by NOK Corporation), and Mobilon (manufactured by Nisshinbo Chemical Inc.), all of which are trade names. Examples thereof further include Isoplast (manufactured by Lubrizol Corporation), Tecoflex (manufactured by Lubrizol Corporation), Superflex 830, 460, 870, 420, and 420NS (polyurethanes manufactured by DKS Co., Ltd.), Hydran AP-40F, WLS-202, and HW-140SF (polyurethanes manufactured by DIC Corporation), Olester UD500 and UD350 (polyurethanes manufactured by Mitsui Chemicals, Inc.), and Takelac W-615, W-6010, W-6020, W-6061, W-405, W-5030, W-5661, W-512A-6, W-635, and WPB-6601 (manufactured by DIC Corporation).

These polyurethanes may be used alone or in combination of two or more thereof.

The resin cover layer may contain various common additives as long as the effects of the present invention are not impaired. Examples of the additives include a heat-resistant stabilizer, a mineral filler, an impact resistance-improving agent, a plasticizer, a lubricant, a metal soap, a light-fast auxiliary agent, and a colorant. The contents of the additives in the resin cover layer can also be appropriately adjusted. Such additives may be derived from resin materials used or can be added separately from polymers.

When the resin cover layer is formed of a plurality of layers, a layer other than the innermost layer preferably includes at least one selected from the group consisting of polyamides, polyesters, and polyolefins. A layer having desired physical properties can be formed by appropriately combining these resins. When the resin cover layer is formed of a plurality of layers, the layer other than the innermost layer more preferably includes a polyamide elastomer or a polyester elastomer, or a polymer alloy of a polyamide elastomer or a polyester elastomer and another polymer from the viewpoint of further enhancing the resilience.

Each of the polymers that can be used as the resin cover layer according to the present invention preferably has a molecular weight of 10,000 to 1,000,000, more preferably has a molecular weight of 20,000 to 500,000, and particularly preferably has a molecular weight of 30,000 to 300,000.

In the present invention, the molecular weight of the polymer means a weight-average molecular weight unless otherwise noted. The weight-average molecular weight can be measured by gel permeation chromatography (GPC) as a molecular weight in terms of polystyrene.

As illustrated in FIG. 2, the resin cover layer 15 in the present invention is preferably formed so as to have a substantially uniform thickness in the longitudinal direction (axial direction) of the flexible tube base 14. The resin cover layer 15 has a thickness of, for example, 0.2 mm to 1.0 mm. An outer diameter D of the flexible tube 3a is appropriately determined according to the purpose and is, for example, 11 to 14 mm. In FIG. 2, the inner layer 17 and the outer layer 18 are formed such that a proportion of a thickness of the inner layer 17 to a total thickness of the resin cover layer 15 and a proportion of a thickness of the outer layer 18 to the total thickness of the resin cover layer 15 change in the axial direction of the flexible tube base 14. Specifically, on one end 14a side (distal end side) of the flexible tube base 14 to be attached to the angle portion 3b, the thickness of the inner layer 17 is larger than the thickness of the outer layer 18 with respect to the total thickness of the resin cover layer 15. The thickness of the inner layer 17 gradually decreases from the one end 14a toward the other end 14b side (proximal end side) to be attached to the main body operating section 5. On the other end 14b side, the thickness of the outer layer 18 is larger than the thickness of the inner layer 17.

In FIG. 2, the proportion of the thickness of the inner layer 17 is the maximum at the one end 14a, and the proportion of the thickness of the outer layer 18 is the maximum at the other end 14b. A ratio of the thickness of the inner layer 17 to the thickness of the outer layer 18 (thickness of inner layer 17:thickness of outer layer 18) can be, for example, 9:1 at the one end 14a, and, for example, 1:9 at the other end 14b. The thicknesses of the two layers are changed such that the ratio of the thickness of the inner layer 17 to the thickness of the outer layer 18 is reversed from the one end 14a to the other end 14b. With this configuration, the flexible tube 3a has a difference in hardness between the one end 14a side and the other end 14b side, and flexibility can be changed in the axial direction such that the one end 14a side is soft and the other end 14b side is hard. The inner layer and the outer layer are preferably formed such that the thickness ratio at the one end is 95:5 to 60:40 (inner layer:outer layer) and the thickness ratio at the other end is 5:95 to 40:60 (inner layer:outer layer).

When the ratio of the thickness of the inner layer 17 to the thickness of the outer layer 18 is within the range of 95:5 to 5:95, the amount of extrusion of a resin that forms a layer having a smaller thickness can also be accurately controlled.

The soft resin used in the inner layer 17 and the hard resin used in the outer layer 18 preferably satisfy the following relations. A difference in 100% modulus, which is an indicator indicating a hardness after molding, is preferably 1 MPa or more and more preferably 3 MPa or more. A difference in melt viscosity at a molding temperature of 150° C. to 300° C., which is an indicator indicating the fluidity of a resin in a molten state, is preferably 2,500 Pa·s or less. With this configuration, the resin cover layer 15 formed of the inner layer 17 and the outer layer 18 reliably achieves both good molding accuracy and the necessary difference in hardness between the distal end side and the proximal end side.

Topcoat Layer

In the flexible tube according to the present invention, the topcoat layer 16 is disposed on an outer periphery of the resin cover layer 15 as needed. Examples of the material of the topcoat layer include, but are not particularly limited to, urethane coatings, acrylic coatings, fluorine coatings, silicone coatings, epoxy coatings, and polyester coatings.

Main purposes of use of the topcoat layer are to protect the surface of the flexible tube, to make the surface of the flexible tube glossy, to impart slidability, and to impart chemical resistance. Therefore, the topcoat layer is preferably formed of a material that has a high modulus of elasticity, that provides a smooth surface, and that has good chemical resistance.

Method for Producing Flexible Tube

Formation of Primer Layer

In the production of a flexible tube according to the present invention, first, a primer layer is formed on an outer periphery of a flexible tube base. The primer layer can be formed by dissolving a compound represented by general formula (1) above in a solvent to prepare a coating liquid; forming a coating film on at least the outer periphery of the flexible tube base by, for example, applying or spraying the coating liquid onto the outer periphery of the flexible tube base or immersing the flexible tube base in the coating liquid; and subsequently drying the coating film by an ordinary method (for example, high-temperature drying at about 100° C. to 170° C.).

Examples of the solvent that can be used for the coating liquid include alcohol solvents such as methanol and ethanol; ketone solvents such as acetone and methyl ethyl ketone; ester solvents such as ethyl acetate; hydrocarbon solvents such as toluene; and liquid mixtures thereof. It is preferable to mix at least any of water or an acid catalyst, such as acetic acid, with the solvents in order to accelerate hydrolysis of, for example, an alkoxy group bound to the silicon atom in the compound represented by general formula (1). The pH of the coating liquid is not particularly limited but may be adjusted as required to be acidic (for example, pH 1 to 4 at 25° C.) or alkaline (for example, pH 9 to 11 at 25° C.) by using a pH adjuster, for example.

The content of the compound represented by general formula (1) in the coating liquid is not particularly limited, can be, for example, 0.01% by mass to 2% by mass, and is preferably 0.05% by mass or more and less than 1.5% by mass and more preferably 0.1% by mass or more and less than 1.0% by mass.

The coating liquid may include, for example, a surfactant and a catalyst besides the compound represented by general formula (1), the solvent, and the pH adjuster. The coating liquid is more preferably constituted by the compound represented by general formula (1) and the solvent.

In the present invention, a portion that is not covered with the primer layer may be present on the outer periphery of the flexible tube base as long as the effects of the present invention are not impaired (that is, a defect may be partially generated in the primer layer).

Prior to the formation of the primer layer, the flexible tube base is preferably cleaned by degreasing with at least any of an acidic solution, an alkaline solution, a surfactant-containing aqueous solution, an organic solvent, or the like. After the cleaning, the flexible tube base is preferably further washed with water or hot water so that an acid, an alkali, a surfactant, and the like decrease from the surface of the base. After the washing with water or hot water, the flexible tube base is preferably dried (for example, at 100° C. for 10 minutes).

Formation of Resin Cover Layer

The production of a flexible tube according to the present invention includes a step of forming a resin cover layer. The step of forming a resin cover layer includes covering, with a resin that includes at least one compound selected from the group consisting of polyamides, polyesters, and polyolefins, the primer layer formed on the outer periphery of the flexible tube base so as to be in contact with the primer layer.

The formation of the resin cover layer will be described using, as an example, a case where the resin cover layer has a two-layer structure.

A flexible tube including a resin cover layer that has a two-layer structure having an inner layer and an outer layer can be produced by, for example, melt-kneading and extruding, around the flexible tube base on which the primer layer has been formed, a first resin material (resin material including at least one compound selected from the group consisting of polyamides, polyesters, and polyolefins) that forms the inner layer and a second resin material that forms the outer layer, thereby covering the flexible tube base.

In an embodiment in which a resin cover layer is formed of one layer or three or more layers, the resin cover layer can also be produced by appropriately changing the layer structure with reference to the method described below.

Figure 3:
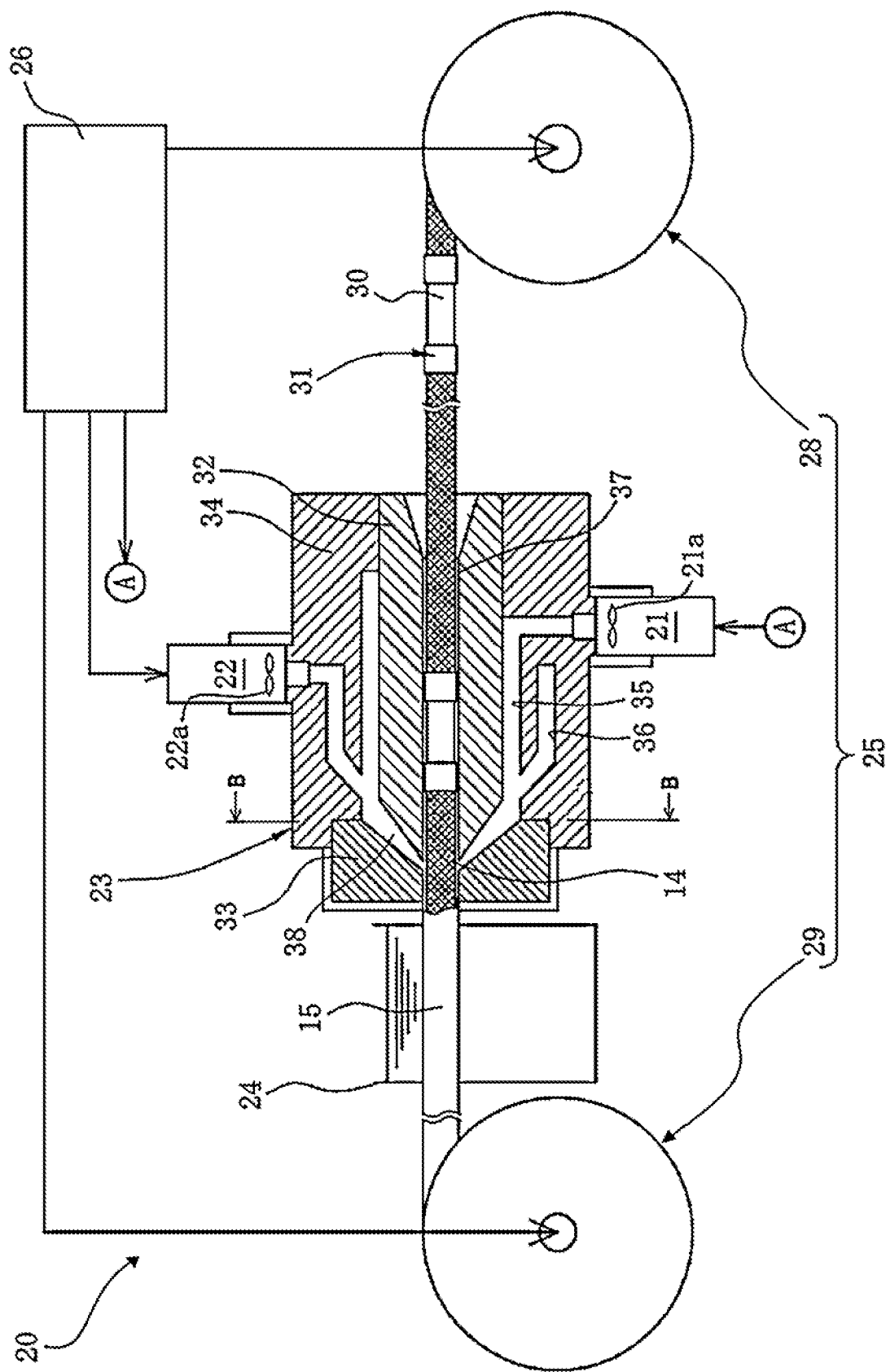
FIG. 3 is a block diagram illustrating a configuration of an apparatus for producing a flexible tube for an endoscope according to an embodiment.
Figure 4:
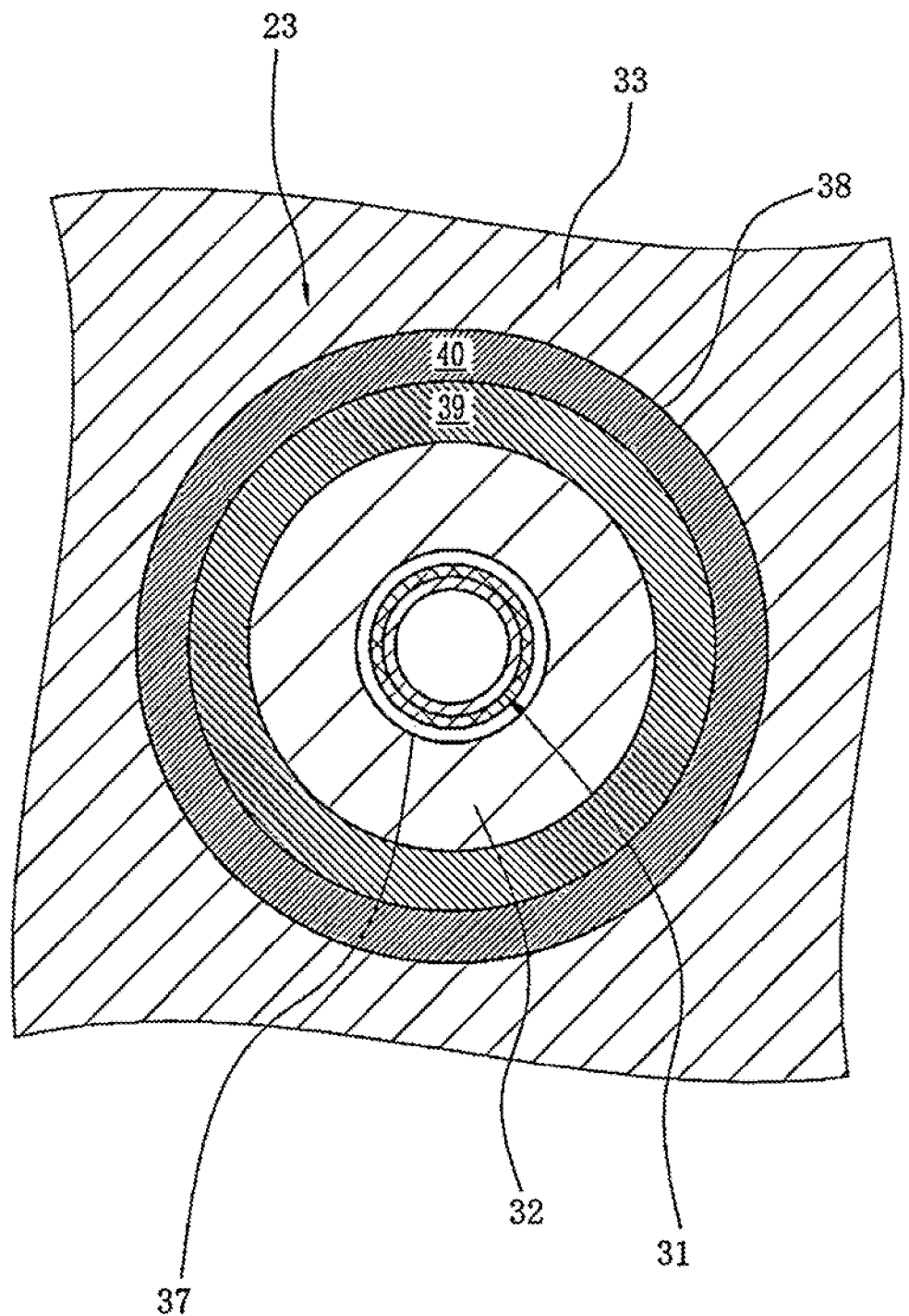
FIG. 4 is a sectional view taken along line B-B in FIG. 3.

An example of a method for forming a resin cover layer of the flexible tube 3a (FIGS. 1 and 2) will be described with reference to FIGS. 3 and 4. In this embodiment, a continuous molding machine is used for molding a resin cover layer 15. It is preferable to use a continuous molding machine 20 that includes well-known extrusion units 21 and 22 including hoppers, screws 21a and 22a, etc.; a head unit 23 configured to mold a resin cover layer 15 so as to cover an outer peripheral surface of a flexible tube base 14; a cooling unit 24; a transport unit 25 (including a supply drum 28 and a take-up drum 29) configured to transport a connected flexible tube base 31 to the head unit 23; and a control unit 26 configured to control the above units. The head unit 23 preferably includes a nipple 32, a die 33, and a support 34 configured to support the nipple 32 and the die 33 in a fixed manner. For example, the apparatus disclosed in FIGS. 3 to 5 of JP2011-72391A can be used as an example of the apparatus having the above configuration.

The inside of the die 33 is preferably heated to a predetermined molding temperature. The molding temperature is preferably set in a range of 150° C. to 300° C. By controlling a temperature of a heating unit in the apparatus by heating, temperatures of a first resin material 39 and a second resin material 40 can be increased. In addition to this, as the rotation speeds of the screws 21a and 22a increase, the temperatures of the first resin material 39 and the second resin material 40 can be further increased to enhance the fluidity of the respective resin materials. In this case, the molding thicknesses of an inner layer 17 and an outer layer 18 can be respectively adjusted by changing the amounts of ejection of the first resin material 39 and the second resin material 40 in the molten state, while a transport speed of the connected flexible tube base 31 is made constant.

A process of molding the resin cover layer 15 on the connected flexible tube base 31 by the continuous molding machine 20 will be described. When the continuous molding machine 20 performs a molding process, the first resin material 39 and the second resin material 40 in the molten state are extruded from the extrusion units 21 and 22, respectively, to the head unit 23. Furthermore, the transport unit 25 operates so that the connected flexible tube base 31 is transported to the head unit 23. At this time, the extrusion units 21 and 22 are in a state of constantly extruding the first resin material 39 and the second resin material 40, respectively, to supply the resin materials 39 and 40 to the head unit 23, and the first resin material 39 and the second resin material 40 that are respectively extruded from the extrusion units 21 and 22 to gates 35 and 36 pass through edges and join to each other, and are supplied, in a stacked state, through a resin passage 38 to a molding passage 37. As a result, a two-layer molded resin cover layer 15 is formed in which an inner layer 17 composed of the first resin material 39 and an outer layer 18 composed of the second resin material 40 are stacked.

The connected flexible tube base 31 includes a plurality of flexible tube bases 14 (each having a primer layer on the outer periphery thereof) that are connected together. While the connected flexible tube base 31 is transferred in the molding passage 37, the resin cover layer 15 is continuously molded on the plurality of flexible tube bases 14. When the resin cover layer 15 is molded from one end 14*a* side (distal end side) of one flexible tube base to the other end 14*b* side (proximal end side) thereof, the thickness of the inner layer 17 is controlled to be large immediately after the extrusion units 21 and 22 start ejection of the resins. The proportion of the outer layer 18 is then gradually increased in an intermediate portion toward the other end 14*b* side. In this manner, the amounts of the resins ejected are preferably controlled such that the resin cover layer 15 has the thickness ratio that changes in a gradient manner.

Joint members 30 each function as a connecting portion of two flexible tube bases 14, and thus the joint members 30 are used for switching the amounts of resins ejected from the extrusion units 21 and 22 by the control unit 26. Specifically, the control unit 26 preferably switches the amounts of resins ejected from the extrusion units 21 and 22 such that the thickness ratio changes from a thickness ratio on the other end 14*b* side (proximal end side) of one flexible tube base 14 to a thickness ratio on one end 14*a* side (distal end side) of a next flexible tube base 14. When the resin cover layer 15 is molded from the one end 14*a* side of the next flexible tube base 14 to the other end 14*b* side thereof, the extrusion units 21 and 22 are preferably similarly controlled such that the thickness of the outer layer gradually increases from the one end side toward the other end side.

The connected flexible tube base 31 on which the resin cover layer 15 has been molded to the rearmost end is removed from the continuous molding machine 20. Subsequently, the joint members 30 are detached from the flexible tube bases 14 to separate the connected flexible tube base 31 into the individual flexible tube bases 14. Next, for each of the separated flexible tube bases 14, the resin cover layer 15 is coated with a topcoat layer 16 to complete flexible tubes 3*a*. The completed flexible tubes 3*a* are transferred to an assembly process of an electronic endoscope.

In the present invention, when the resin cover layer is formed of formed of a plurality of layers, a functional layer may be disposed between layers that form the plurality of layers.

An electronic endoscope configured to observe an image of the condition of a subject captured by using an imaging device has been described with reference to the drawings by way of an example. However, the present invention is not limited thereto and is also applicable to an endoscope configured to examine the condition of a subject by employing an optical image guide.

The flexible tube according to the present invention is widely applicable to endoscopic medical devices. For example, the flexible tube according to the present invention is applicable to an endoscope equipped with a clip or a wire at the distal end thereof or to an instrument equipped with a basket or a brush. Note that the term "endoscopic medical device" is meant to broadly include, besides the above-described medical devices that include an endoscope as a basic structure, medical devices and diagnosis and treatment devices that include an insertion section having flexibility and that are introduced into the body and used, such as remote-controlled medical devices.

An endoscopic medical device according to the present invention includes the flexible tube for an endoscope according to the present invention, the flexible tube being incorporated in an insertion section of the endoscopic medical device. That is, a method for producing an endoscopic medical device according to the present invention includes incorporating the flexible tube for an endoscope according to the present invention into an insertion section of an endoscopic medical device.

EXAMPLES

Hereafter, the present invention will be described in more detail by way of Examples. However, it is to be understood that the present invention is not limited to these Examples.

EXAMPLES AND COMPARATIVE EXAMPLES

Production of Flexible Tube for Endoscope

Flexible tubes having the structure illustrated in FIG. 2 were produced. The resin cover layers had a single-layer structure as shown in tables below.

Flexible Tube Base

Flexible tube bases were prepared. Each of the flexible tube bases had a form in which a spiral tube 11 was formed by using a metal strip 11*a* made of stainless steel, and the spiral tube 11 was covered with a tubular mesh 12 obtained by weaving stainless steel fibers. The flexible tube base has a length of 80 cm and a diameter of 12 mm. This stainless steel flexible tube base has a passivation layer on a surface thereof, the passivation layer being formed by annealing treatment (heating treatment) in the formation of the spiral tube and the tubular mesh.

Preparation of Coating Liquid for Forming Primer Layer

A solution having a ratio water/ethanol of 5/75 on a mass basis was prepared. Each of the compounds shown in the tables below was separately dissolved in the solution so as to have a concentration of 5.0 g/kg. The resulting solutions were used as coating liquids for forming primer layers.

Formation of Primer Layer

The flexible tube bases were cleaned by immersing in a 7.5% aqueous solution of sodium hydroxide at 60° C. for one minute (degreasing/cleaning step). Subsequently, the flexible tube bases were rinsed with distilled water and then dried in an oven at 100° C. for 10 minutes. The cleaned flexible tube bases were immersed in the above-prepared coating liquids for forming primer layers at room temperature for one minute and then dried in an oven at 160° C. for 10 minutes. Thus, flexible tube bases each having a primer layer on the outer periphery thereof (the surface to be covered with a resin) were prepared.

Formation of Resin Cover Layer

The outer peripheries of the flexible tube bases having the primer layer thereon were covered with the resins shown in the tables below by extrusion (molding temperature: 200° C.) to produce flexible tubes for endoscopes, the flexible tubes having a resin cover layer. The resin cover layer had a thickness of 0.4 mm.

Evaluation

Bending durability and peracetic acid resistance of each of the above-produced flexible tubes for endoscopes were evaluated as described in Test Examples below. The results are summarized in the tables below. Test Nos. 101 to 140 correspond to flexible tubes for endoscopes according to the present invention, and Test Nos. c01 to c18 correspond to flexible tubes for endoscopes of Comparative Examples.

Test Example 1

Evaluation of Bending Durability

The above-produced flexible tube (length: 80 cm) for an endoscope was brought into contact, in a U shape, with a semicircular portion of a pulley with a diameter of 10 cm and reciprocated by alternately pulling one end and the other end of the U-shaped flexible tube for an endoscope. This reciprocating motion was performed such that a portion of the flexible tube for an endoscope, the portion having a length of 44.3 cm and excluding portions each having a length of 17.85 cm from both ends of the flexible tube, successively formed the apex of the U shape while being in contact with the pulley. The number of reciprocating motions in which a crease, floating, tearing, or separation of a resin occurred was evaluated in accordance with the evaluation criteria described below. In the present invention, "C" or higher is satisfactory.

Evaluation Criteria for Bending Durability
A: 10,000 times or more
B: 1,000 times or more and less than 10,000 times
C: 100 times or more and less than 1,000 times
D: less than 100 times Test Example 2

Evaluation of Peracetic Acid Resistance

Both ends of the above-produced flexible tube for an endoscope were capped with Teflon (registered trademark) plugs, and the flexible tube was disinfected by immersing in a 0.3% aqueous peracetic acid solution at 55° C. for 150 hours. After the disinfection, the surface was sufficiently washed with water to prepare a flexible tube for an endoscope after immersion in the aqueous peracetic acid solution. For each of the flexible tube for an endoscope before disinfection (flexible tube for an endoscope, the flexible tube not being subjected to disinfection) and the flexible tube for an endoscope after disinfection, a peeling test was conducted as describe below to measure a 90° peel strength $PS_B$ before disinfection and a 90° peel strength $PS_A$ after disinfection. A ratio ($PS_A/PS_B \times 100$) of the 90° peel strength $PS_A$ after disinfection to the 90° peel strength $PS_B$ before disinfection was determined, and an evaluation was performed in accordance with the criteria described below. In the present invention, "C" or higher is satisfactory.

Peeling Test

For the resin cover layer of the flexible tube for an endoscope, a cut having a length of 5 cm and a width of 1 cm and extending in the axial direction of the flexible tube was formed in a direction perpendicular to the resin cover layer such that the cut reached the flexible tube base. For one end of this cut, a cut was further formed in the width direction to form a holding portion for the peeing test. The length direction of the cut formed above is the same as the axial direction of the flexible tube, and the cut has a width of 1 cm on the outer peripheral surface of the resin cover layer. A 90° peel strength between the flexible tube base and the resin cover layer was measured by holding the end of the above-formed cut with a width of 1 cm and peeling off the resin cover layer in the axial direction of the flexible tube at a constant speed while an angle between the flexible tube base and the peeled resin cover layer was maintained at 90°. The peel strength is a value measured with a force gauge and is expressed in units of N/cm. For all the flexible tubes, the 90° peel strength was measured under the same conditions.

Evaluation Criteria for Peracetic Acid Resistance
A: 80% or more
B: 60% or more and less than 80%
C: 40% or more and less than 60%
D: less than 40%

TABLE 1-1

| | | No. | | | | | | | | | | | | | | | |
|---|---|---|---|---|---|---|---|---|---|---|---|---|---|---|---|---|---|
| | | 101 | 102 | 103 | 104 | 105 | 106 | 107 | 108 | 109 | 110 | 111 | 112 | 113 | 114 | 115 |
| Structure | Resin cover layer | PA1 | PA1 | PA1 | PA1 | PA1 | PA1 | PA1 | PA1 | PA1 | PA1 | PA1 | PA1 | PA2 | PA3 | PA4 |
| | Compound in primer layer | S-1 | S-2 | S-3 | S-4 | S-7 | S-8 | S-9 | S-10 | S-19 | S-24 | S-29 | S-33 | S-2 | S-2 | S-2 |
| Evaluation | Bending durability | B | A | B | B | A | B | A | A | A | B | B | B | A | A | A |
| | Peracetic acid resistance | C | A | A | A | A | A | B | B | A | A | A | A | A | A | A |

| | | No. | | | | | | | | | | | | | | | |
|---|---|---|---|---|---|---|---|---|---|---|---|---|---|---|---|---|---|
| | | 116 | 117 | 118 | 119 | 120 | 121 | 122 | 123 | 124 | 125 | 126 | 127 | 128 | 129 | 130 |
| Structure | Resin cover layer | PEs1 | PEs1 | PEs1 | PEs1 | PEs1 | PEs1 | PEs1 | PEs1 | PEs1 | PEs1 | PEs1 | PEs1 | PEs2 | PEs3 | PEs4 |
| | Compound in primer layer | S-1 | S-2 | S-3 | S-4 | S-7 | S-8 | S-9 | S-10 | S-19 | S-24 | S-29 | S-33 | S-2 | S-2 | S-2 |
| Evaluation | Bending durability | A | A | B | B | A | B | A | A | A | B | B | B | A | A | A |
| | Peracetic acid resistance | C | A | B | B | A | B | B | B | A | B | B | B | A | A | A |

TABLE 1-1-continued

| | | No. | | | | | | | | | |
|---|---|---|---|---|---|---|---|---|---|---|---|
| | | 131 | 132 | 133 | 134 | 135 | 136 | 137 | 138 | 139 | 140 |
| Structure | Resin cover layer | PO1 | PO1 | PO1 | PO1 | PO1 | PO1 | PO1 | PO1 | PO1 | PO1 |
| | Compound in primer layer | S-1 | S-2 | S-3 | S-4 | S-7 | S-8 | S-9 | S-10 | S-19 | S-24 |
| Evaluation | Bending durability | C | A | C | C | A | C | B | B | A | C |
| | Peracetic acid resistance | A | A | A | A | A | A | A | A | A | A |

TABLE 1-2

| | | No. | | | | | | | | | | | | | | | | | |
|---|---|---|---|---|---|---|---|---|---|---|---|---|---|---|---|---|---|---|---|
| | | c01 | c02 | c03 | c04 | c05 | c06 | c07 | c08 | c09 | c10 | c11 | c12 | c13 | c14 | c15 | c16 | c17 | c18 |
| Structure | Resin cover layer | PA1 | PEs1 | PO1 | PA1 | PA1 | PA1 | PA1 | PA1 | PEs1 | PEs1 | PEs1 | PEs1 | PEs1 | PO1 | PO1 | PO1 | PO1 | PO1 |
| | Compound in primer layer | — | — | — | R-1 | R-2 | R-3 | R-4 | R-5 | R-1 | R-2 | R-3 | R-4 | R-5 | R-1 | R-2 | R-3 | R-4 | R-5 |
| Evaluation | Bending durability | D | D | D | C | D | C | C | C | C | D | C | C | C | D | D | D | D | D |
| | Peracetic acid resistance | D | D | D | D | D | D | D | D | D | D | D | D | D | C | D | C | C | C |

Note in Tables
Cover Layer Resin
(1) Polyamide
  PA1: DAIAMID L1940 (trade name, manufactured by Daicel-Evonik Ltd., polyamide 12, MVR=8 cm$^3$/10 min)
  PA2: VESTAMID Terra DS16 (trade name, manufactured by Daicel-Evonik Ltd., polyamide 1010, MVR=20 cm$^3$/10 min)
  PA3: Rilsan BMN O (trade name, manufactured by Arkema Inc., polyamide 11, MVR=36 cm$^3$/10 min)
  PA4: PEBAX 7233 (trade name, manufactured by Arkema Inc., polyether block amide, MVR=4 cm$^3$/10 min)
(2) Polyester
  PEs1: PELPRENE P-70B (trade name, manufactured by Toyobo Co., Ltd., polyester-based elastomer, MVR=20 cm$^3$/10 min)
  PEs2: PELPRENE S-3001 (trade name, manufactured by Toyobo Co., Ltd., thermoplastic polyester-based elastomer, MVR=16 cm$^3$/10 min)
  PEs3: PRIMALLOY B1942 (trade name, manufactured by Mitsubishi Chemical Corporation, thermoplastic polyester-based elastomer, MVR=59 cm$^3$/10 min)
  PEs4: NOVADURAN 5505S (trade name, manufactured by Mitsubishi Engineering-Plastics Corporation, polybutylene terephthalate, MVR=25 cm$^3$/10 min)
(3) Polyolefin
  PO1: SARLINK 3145D (trade name, manufactured by Toyobo Co., Ltd., dynamically crosslinked thermoplastic elastomer in which dynamically crosslinked EPDM (ethylene-propylene-diene ternary copolymer) rubber particles are finely dispersed in a PP (polypropylene) matrix, MVR=54 cm$^3$/10 min)
Compound in Primer Layer
  S-1 to S-4, S-7 to S-10, S-19, S-24, S-29, and S-33:
    Compounds S-1 to S-4, S-7 to S-10, S-19, S-24, S-29, and S-33 shown as the specific examples above R-1: Vinyltrimethoxysilane
R-2: Tetraethoxysilane
R-3: Propyltrimethoxysilane (manufactured by Gelest, Inc., trade name "SIP6918.0")
R-4: 2-Cyanoethyltrimethoxysilane (manufactured by Gelest, Inc., trade name "SIC2445.0")
R-5: 3-Chloropropyltrimethoxysilane (manufactured by Gelest, Inc., trade name "SIC2410.0")

As shown in Table 1, each of the comparative flexible tube Nos. c01 to c03 for endoscopes, in which the outer periphery of the flexible tube base was covered with a resin cover layer specified in the present invention without providing a primer layer, was poor in both properties of bending durability and peracetic acid resistance. The comparative flexible tube Nos. c04 to c18 for endoscopes each have a primer layer containing an amino group-free silane coupling agent, which is not included in general formula (1), between the flexible tube base and a resin cover layer specified in the present invention. The comparative flexible tube Nos. c04 to c18 for endoscopes were each poor in at least one property of bending durability or peracetic acid resistance, although the results depended on the type of resin included in the resin cover layer.

It was found that, in contrast, each of the flexible tube Nos. 101 to 140 for endoscopes, in which a primer layer contained a compound represented by general formula (1) and a resin cover layer in contact with the primer layer included at least one compound selected from the group consisting of polyamides, polyesters, and polyolefins, could sufficiently maintain the adhesiveness between the flexible tube base and the resin cover layer even when a bending operation was repeated or when the flexible tube was subjected to disinfection treatment with peracetic acid, and had good bending durability and good peracetic acid resistance.

The present invention has been described together with embodiments thereof. However, we do not intend to limit our invention in any of the details of the description unless otherwise specified. We believe that the invention should be broadly construed without departing from the spirit and scope of the invention as defined by the appended claims.

REFERENCE SIGNS LIST 2 electronic endoscope (endoscope)
3 insertion section
3a flexible tube
3b angle portion
3c tip portion
5 main body operating section
6 universal cord
11 spiral tube
11a metal strip
12 tubular mesh
13 cap
14 flexible tube base
14a distal end side
14b proximal end side
15 resin cover layer
16 topcoat layer
17 inner layer
18 outer layer
X angle portion 3b side (soft)
Y main body operating section 5 side (hard)
20 continuous molding machine (production apparatus)
21, 22 extrusion unit
21a screw
22a screw
23 head unit
24 cooling unit
25 transport unit
26 control unit
28 supply drum
29 take-up drum
30 joint member
31 connected flexible tube base
32 nipple
33 die
34 support
35, 36 gate
37 molding passage
38 resin passage
39 first resin material (soft material)
40 second resin material (hard material)

What is claimed is:

1. A flexible tube for an endoscope, the flexible tube comprising:
a flexible tube base containing metal as a constituent material;
a resin cover layer that covers an outer periphery of the flexible tube base; and
a primer layer that includes a compound represented by general formula (1) and that is disposed between the flexible tube base and the resin cover layer,
wherein the resin cover layer includes at least one compound selected from the group consisting of polyamides, polyesters, and polyolefins at least on a side of the resin cover layer in contact with the primer layer:

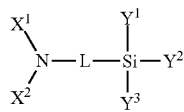

General formula (1)

where $X^1$ and $X^2$ each represent a hydrogen atom, an alkyl group, a cycloalkyl group, an alkenyl group, an aryl group, an acyl group, an alkoxycarbonyl group, or a carbamoyl group;
$Y^1$ represents a hydroxy group or an alkoxy group;
$Y^2$ and $Y^3$ each represent a hydrogen atom, a halogen atom, a hydroxy group, an alkoxy group, an oxime group, or an alkyl group;
L represents a single bond, a divalent group selected from the group consisting of alkylene groups, arylene groups, and —O—, or a divalent group which is a combination of two or more selected from the group consisting of the aforementioned divalent groups; and
$X^1$ and $X^2$ may be linked to each other to form a ring.

2. The flexible tube for an endoscope according to claim 1, wherein the compound represented by general formula (1) has two or more nitrogen atoms.

3. The flexible tube for an endoscope according to claim 1, wherein the metal that constitutes the flexible tube base is stainless steel.

4. The flexible tube for an endoscope according to claim 1, wherein the metal that constitutes the flexible tube base has a passivation film on a surface thereof.

5. The flexible tube for an endoscope according to claim 1, wherein the resin cover layer has a single-layer structure or a multilayer structure and includes at least one compound selected from the group consisting of polyamides, polyesters, and polyolefins in a layer in contact with the primer layer.

6. The flexible tube for an endoscope according to claim 1,
wherein the resin cover layer has a two-layer structure, and
a ratio of a thickness of an inner layer to a thickness of an outer layer of the two-layer structure changes in a gradient manner in an axial direction of the flexible tube base.

7. The flexible tube for an endoscope according to claim 6, wherein the ratio of the thickness of the inner layer to the thickness of the outer layer is inner layer:outer layer=95:5 to 60:40 at one end of the flexible tube for an endoscope and is inner layer:outer layer=5:95 to 40:60 at the other end.

8. An endoscopic medical device comprising the flexible tube for an endoscope according to claim 1.

9. A method for producing a flexible tube for an endoscope, the method comprising:
a step of forming, on at least an outer periphery of a flexible tube base that contains metal as a constituent material, a primer layer that includes a compound represented by general formula (1); and
a step of forming a resin cover layer, the step including covering, with a resin that includes at least one compound selected from the group consisting of polyamides, polyesters, and polyolefins, the primer layer formed on the outer periphery of the flexible tube base so that the resin cover layer is in contact with the primer layer:

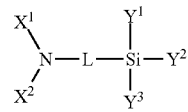

General formula (1)

where $X^1$ and $X^2$ each represent a hydrogen atom, an alkyl group, a cycloalkyl group, an alkenyl group, an aryl group, an acyl group, an alkoxycarbonyl group, or a carbamoyl group;

$Y^1$ represents a hydroxy group or an alkoxy group;

$Y^2$ and $Y^3$ each represent a hydrogen atom, a halogen atom, a hydroxy group, an alkoxy group, an oxime group, or an alkyl group;

L represents a single bond, a divalent group selected from the group consisting of alkylene groups, arylene groups, and —O—, or a divalent group which is a combination of two or more selected from the group consisting of the aforementioned divalent groups; and $X^1$ and $X^2$ may be linked to each other to form a ring.

10. The method for producing a flexible tube for an endoscope according to claim 9, wherein the resin cover layer has a two-layer structure, at least an inner layer of the two-layer structure includes at least one compound selected from the group consisting of polyamides, polyesters, and polyolefins, and a ratio of a thickness of the inner layer to a thickness of an outer layer of the two-layer structure changes in a gradient manner in an axial direction of the flexible tube base.

11. A method for producing an endoscopic medical device, comprising:

a step of producing a flexible tube for an endoscope by the method for producing a flexible tube for an endoscope according to claim 9; and a step of incorporating the produced flexible tube for an endoscope into an insertion section of an endoscopic medical device.

12. A method for producing an endoscopic medical device, comprising incorporating the flexible tube for an endoscope according to claim 1 into an insertion section of an endoscopic medical device.

* * * * *